United States Patent
Rioux

(10) Patent No.: US 11,278,029 B2
(45) Date of Patent: Mar. 22, 2022

(54) **ANTIFUNGAL *METHYLOBACTERIUM* COMPOSITIONS AND METHODS OF USE**

(71) Applicant: NEWLEAF SYMBIOTICS, INC., St. Louis, MO (US)

(72) Inventor: Renée Rioux, Morrisville, NC (US)

(73) Assignee: NewLeaf Symbiotics, Inc., St. Louis, MO (US)

(*) Notice: Subject to any disclaimer, the term of this patent is extended or adjusted under 35 U.S.C. 154(b) by 717 days.

(21) Appl. No.: 15/580,208

(22) PCT Filed: Jun. 10, 2016

(86) PCT No.: PCT/US2016/036968
§ 371 (c)(1),
(2) Date: Sep. 10, 2018

(87) PCT Pub. No.: WO2016/201284
PCT Pub. Date: Dec. 15, 2016

(65) Prior Publication Data
US 2018/0295841 A1   Oct. 18, 2018

Related U.S. Application Data

(60) Provisional application No. 62/173,789, filed on Jun. 10, 2015.

(51) Int. Cl.
| A01N 63/30 | (2020.01) |
| C12N 1/20 | (2006.01) |
| A01N 63/20 | (2020.01) |
| A01N 25/04 | (2006.01) |
| C12R 1/26 | (2006.01) |

(52) U.S. Cl.
CPC ............. *A01N 63/30* (2020.01); *A01N 25/04* (2013.01); *A01N 63/20* (2020.01); *C12N 1/20* (2013.01); *C12N 1/205* (2021.05); *C12R 2001/26* (2021.05)

(58) Field of Classification Search
CPC ........ A01N 63/10; A01N 63/00; A01N 25/04; A01N 63/30; A01N 63/20; C12N 1/20; C12N 1/205; C12R 1/26; C12R 2001/26
See application file for complete search history.

(56) References Cited

U.S. PATENT DOCUMENTS

| 6,014,451 A | 1/2000 | Berry et al. |
| 6,133,196 A * | 10/2000 | Ocamb ................. A01N 63/30 504/100 |
| 9,181,541 B2 | 11/2015 | Bogosian |
| 9,845,462 B2 | 12/2017 | Bogosian |
| 10,098,353 B2 | 10/2018 | Breakfield et al. |
| 10,111,438 B2 | 10/2018 | Floro et al. |
| 10,212,939 B2 | 2/2019 | Floro et al. |
| 10,287,544 B2 | 5/2019 | Bogosian |
| 10,368,547 B2 | 8/2019 | Floro et al. |
| 10,448,645 B2 * | 10/2019 | Breakfield ............. A01N 63/00 |
| 10,450,556 B2 | 10/2019 | Bogosian |
| 10,716,307 B2 | 7/2020 | Breakfield et al. |
| 10,757,946 B2 | 9/2020 | Allen et al. |
| 2008/0148432 A1 | 6/2008 | Abad |
| 2011/0053771 A1* | 3/2011 | Goodwin ................. C05G 3/60 504/100 |
| 2014/0147425 A1 | 5/2014 | Henn et al. |
| 2015/0044327 A1* | 2/2015 | Feinberg .................. C12N 1/20 426/2 |
| 2015/0337256 A1 | 11/2015 | Bogosian |
| 2016/0073641 A1 | 3/2016 | Allen et al. |
| 2016/0120188 A1 | 5/2016 | Bogosian |
| 2016/0295868 A1 | 10/2016 | Jones et al. |
| 2016/0302423 A1 | 10/2016 | Jones et al. |
| 2016/0302424 A1 | 10/2016 | DiDonato et al. |
| 2016/0302425 A1 | 10/2016 | DiDonato et al. |
| 2017/0086464 A1 | 3/2017 | Floro et al. |
| 2017/0135352 A1 | 5/2017 | Breakfield et al. |
| 2017/0164618 A1 | 6/2017 | Breakfield et al. |
| 2017/0238553 A1 | 8/2017 | Jones et al. |
| 2018/0142230 A1 | 5/2018 | Bogosian |
| 2018/0295841 A1 | 10/2018 | Rioux |
| 2019/0021334 A1 | 1/2019 | DiDonato Floro et al. |
| 2019/0116803 A1 | 4/2019 | DiDonato Floro et al. |
| 2019/0241865 A1 | 8/2019 | Bogosian |
| 2019/0297895 A1 | 10/2019 | Floro et al. |
| 2019/0364905 A1 | 12/2019 | Rioux et al. |
| 2020/0315181 A1 | 10/2020 | Breakfield et al. |
| 2020/0318095 A1 | 10/2020 | Bogosian |

FOREIGN PATENT DOCUMENTS

| CA | 2183275 A1 | 2/1998 |
| CN | 101028008 A | 9/2007 |
| CN | 104508118 A | 4/2015 |
| WO | 2013181610 A1 | 12/2013 |
| WO | 2015/085063 A1 | 6/2015 |

(Continued)

OTHER PUBLICATIONS

International Search Report and Written Opinion for PCT/US2016/36968 dated Dec. 7, 2016.
Madhaiyan et al., "Growth Promotion and Induction of Systemic Resistance in Rice Cultivar Co-47 (*Oryza sativa* L.) by *Methylobacterium* spp.", Bot. Bull. Acad. Sin., 2004, pp. 315-324, vol. 45.
Madhaiyan et al., "Pink Pigmented Facultative Methylotrophic Bacteria (PPFMs): Introduction to Current Concepts", Korean J. Soil Sci. Fert., 2004, pp. 266-287, vol. 37, No. 4.
Madhaiyan et al., "Plant Growth-Promoting Methylobacterium Induces Defense Responses in Groundnut (*Arachis hypogaea* L.) Compared with Rot Pathogens", Current Microbiology, 2006, pp. 270-276, vol. 53.
Poorniammal et al., "In Vitro Biocontrol Activity of Methylobacterium Extorquens Against Fungal Pathogens", International Journal of Plant Protection, 2009, pp. 59-62, vol. 2, No. 1.

(Continued)

*Primary Examiner* — Sue X Liu
*Assistant Examiner* — Andriae M Holt
(74) *Attorney, Agent, or Firm* — Stinson LLP

(57) ABSTRACT

Compositions comprising *Methylobacterium* with anti-fungal activity, methods for controlling plant pathogenic fungi, and methods of making the compositions are provided.

23 Claims, 3 Drawing Sheets
Specification includes a Sequence Listing.

(56) References Cited

FOREIGN PATENT DOCUMENTS

| WO | 2015085115 A1 | 6/2015 |
| WO | 2015085116 A1 | 6/2015 |
| WO | 2015085117 A1 | 6/2015 |
| WO | 2015/142393 A1 | 9/2015 |
| WO | 2015/200902 A2 | 12/2015 |
| WO | 2016/069564 A1 | 5/2016 |
| WO | 2016/201284 A2 | 12/2016 |
| WO | 2018106899 A1 | 6/2018 |
| WO | 2020117689 A1 | 6/2020 |
| WO | 2020117690 A1 | 6/2020 |

OTHER PUBLICATIONS

Savitha, "Studies On Pink Pigmented Facultative Methylotrophs Of Major Chilli Growing Areas of North Karnataka", Jun. 1, 2015, pp. 1-139, retrieved from: http://krishikosh.egranth.ac.in/bitstream/69836/1/th10680.pdf.

International Search Report and Written Opinion for PCT/US2016/036968 dated Dec. 7, 2016.

International Search Report and Written Opinion for PCT/US2017/065081 dated Mar. 12, 2018.

Menpara et al., "Endophytic Bacteria-Unexplored Reservoir of Antimicrobials for Combating Microbial Pathogens", Microbial Pathogens and Strategies for Combating them: Science, Technology and Education, Dec. 1, 2013, pp. 1095-1103, vol. 2.

Nascimento et al., "Endophytic Bacteria from Piper Tuberculatum Jacq.: Isolation, Molecular Characterization, and in Vitro Screening for the Control of *Fusarium solani* f. sp. *piperis*, the Casual Agent of Root Rot Disease in Black Pepper (*Piper nigrum* L.)", Genetics and Molecular Research, Jan. 1, 2015, pp. 7567-7577, vol. 14, No. 3.

Tani et al., "High-Throughput Identification and Screening of Novel *Methylobacterium* Species Using Whole-Cell MALDI-TOF/MS Analysis", PLoS ONE, Jul. 12, 2012, pp. 1-13, vol. 7, No. 7.

Ardanov et al., "Effects of *Methylobacterium* sp. on emergence, yield, and disease prevalence in three cultivars of potato (*Solanum tuberosum* L.) were associated with the Shift in Endophytic Microbial Community", Plant and Soil, May 2015, pp. 299-310, vol. 405, No. 1, Kluwer Academic Publishers.

Extended European Search Report for EP17877804.9 dated Jun. 26, 2020.

Schlaeppi et al., "The Plant Microbiome at Work", MPMI vol. 28, No. 3, 2015, p. 217; http://dx.doi.org/10.1094/MPMI-10-14-0334-FI.

Tani et al. Supplemental Data S2 Table downloaded from the internet site https://doi.org/10.1371/journal.pone.0129509.s005 on Nov. 20, 2020, and reformatted for conversion to PDF.

Tani et al, "*Methylobacterium* Species Promoting Rice and Barley Growth and Interaction Specificity Revealed with Whole-Cell Matrix-Assisted Laser Desporption/Ionization-Time-of-Flight Mass Spectrometry (MALDI-TOF/MS) Analysis", PLOS One, Jun. 8, 2015, pp. 2-15.

\* cited by examiner

FIGURE 1A, B, C, D, E

ANTIFUNGAL *METHYLOBACTERIUM* COMPOSITIONS AND METHODS OF USE

CROSS-REFERENCE TO RELATED APPLICATIONS

This is a U.S. National Phase application of PCT/US2016/036968, filed on Jun. 10, 2016, which claims the benefit of U.S. Provisional Patent Application No. 62/173,789, filed Jun. 10, 2015, both of which are incorporated herein by reference in their entireties.

SEQUENCE LISTING STATEMENT

A sequence listing containing the file named 53907_153532_SL.txt which is 14,824,692 bytes (measured in MS-Windows®) and created on Jun. 10, 2016, comprises 9,188 sequences, is provided herewith via the USPTO's EFS system, and is incorporated herein by reference in its entirety.

BACKGROUND

One-carbon organic compounds such as methane and methanol are found extensively in nature, and are utilized as carbon sources by bacteria classified as methanotrophs and methylotrophs. Methanotrophic bacteria include species in the genera *Methylobacter, Methylomonas, Methylomicrobium, Methylococcus, Methylosinus, Methylocystis, Methylosphaera, Methylocaldum*, and *Methylocella* (Lidstrom, 2006). Methanotrophs possess the enzyme methane monooxygenase that incorporates an atom of oxygen from $O_2$ into methane, forming methanol. All methanotrophs are obligate one-carbon utilizers that are unable to use compounds containing carbon-carbon bonds. Methylotrophs, on the other hand, can also utilize more complex organic compounds, such as organic acids, higher alcohols, sugars, and the like. Thus, methylotrophic bacteria are facultative methylotrophs. Methylotrophic bacteria include species in the genera *Methylobacterium, Hyphomicrobium, Methylophilus, Methylobacillus, Methylophaga, Aminobacter, Methylorhabdus, Methylopila, Methylosulfonomonas, Marinosulfonomonas, Paracoccus, Xanthobacter, Ancylobacter* (also known as *Microcyclus*), *Thiobacillus, Rhodopseudomonas, Rhodobacter, Acetobacter, Bacillus, Mycobacterium, Arthobacter*, and *Nocardia* (Lidstrom, 2006).

Most methylotrophic bacteria of the genus *Methylobacterium* are pink-pigmented. They are conventionally referred to as PPFM bacteria, being pink-pigmented facultative methylotrophs. Green (2005, 2006) identified twelve validated species in the genus *Methylobacterium*, specifically *M. aminovorans, M. chloromethanicum, M. dichloromethanicum, M. extorquens, M. fujisawaense, M. mesophilicum, M. organophilum, M. radiotolerans, M. rhodesianum, M. rhodinum, M. thiocyanatum*, and *M. zatmanii*. However, *M. nidulans* is a nitrogen-fixing *Methylobacterium* that is not a PPFM (Sy et al., 2001). *Methylobacterium* are ubiquitous in nature, being found in soil, dust, fresh water, sediments, and leaf surfaces, as well as in industrial and clinical environments (Green, 2006).

*Fusarium graminearum* is the causal agent of *Fusarium* head blight (FHB) on wheat, barley, and other cereals. This pathogen is also responsible for ear and stalk rot in corn. In addition to causing significant reductions in yield and grain quality, *F. graminearum* produces harmful mycotoxins that are a major concern in the animal feed industry. Furthermore, there is an increasing problem in farming with fungal pathogens such as *F. graminearum* becoming resistant to a wide range of chemical fungicides. Thus there exists a need in the farming and animal feed industries for the development of effective new approaches for control of fungal pathogens.

*Rhizoctonia solani* is a polyphagous basidiomycete fungus, with a broad host range that encompasses many economically important monocot and dicot plants. *R. solani* is known primarily as a damping off pathogen because it attacks young seedlings, either preventing their emergence from the soil or killing them shortly after emergence. This soil-borne pathogen persists for years in soil both by surviving as a saprophyte and by forming dormant survival structures known as sclerotia. Aside from fumigation, which is often not feasible due to expense and environmental concerns, multi-year rotations away from host crops, chemical seed treatment, and cultural practices that promote plant health are preferred methods of disease management. None of these treatments, however, is completely effective, particularly in cool, wet years that promote pathogen growth and stress seedling health.

*Sclerotinia sclerotiorum* is a polyphagous ascomycete fungus, with a host range that encompasses thousands of dicot plants. White mold, caused by *S. sclerotiorum*, on soybean and other leguminous crops is of particular agronomic importance. Under cool, moist environmental conditions, this disease causes premature senescence and drastically reduced yields. There is no available complete genetic resistance to white mold and partial resistance is only marginally effective. Further, fungicide applications specifically for white mold are only applied in years when disease is highly likely and must be applied within a narrow window to provide effective protection.

Sudden death syndrome of soybean first appeared in Arkansas in 1971 and has since spread to states across the Midwestern region of the United States (Rupe et al. 1991). The disease is caused by the soil-borne fungus *Fusarium virguliforme*, previously known as *Fusarium solani* f. sp. glycines, and is exacerbated by conditions of high soil moisture and soil compaction (Ringler, 1995; Roy et al. 1997). Symptoms of SDS include a mosaic-like appearance of leaf tissue in which main veins remain green while other leaf areas become chlorotic or necrotic, reddish discoloration of xylem tissue, blackening or rotting of root tissue, and significant reductions to overall plant health and yield. From 1994-2010, soybean yield losses to diseases caused by *Fusarium* species were estimated at c. 36.2 million bushels/year and the majority of these losses were attributed to *F. virguliforme* (Wrather et al. 2010).

Lack of effective disease management measures is the primary reason that the majority of soybean yield losses to *Fusarium* spp. during this time can be attributed to *F. virguliforme*. Due to the soilborne nature of this disease, there are few options to eradicate the pathogen once it has been introduced. Consequently, cultural methods that promote plant health, resistant cultivars, and seed treatment are preferred SDS management tactics. None of these tactics provides complete control of the disease, and options for resistant cultivars and seed treatments labeled for SDS are limited. Further, iLevo (fluopyram; Bayer CropScience), the primary seed treatment option for SDS, is expensive and has a negative impact on early-season plant health. Applications of PPFM bacteria in conjunction with other strategies to combat SDS provide an attractive method for improving suppression of this economically important disease and combating the significant yield losses to which it contributes.

SUMMARY

Provided herein are compositions comprising *Methylobacterium* that inhibit growth of a plant pathogenic fungus, methods of using the compositions to control fungal infections of plants, plant parts, and plants derived therefrom, and methods of making the compositions. Such *Methylobacterium* that inhibit growth of a plant pathogenic fungus are in certain instances referred to herein as "*Methylobacterium* that inhibit plant pathogenic fungi" or, in certain contexts, as simply "*Methylobacterium*". In certain embodiments, *Methylobacterium* that inhibit growth of a plant pathogenic fungus can be distinguished from other *Methylobacterium* that do not inhibit plant pathogenic fungi by assaying for the ability of the *Methylobacterium* to inhibit fungal disease in a plant or isolated plant part.

Provided herein are compositions comprising a mono- or co-culture of *Methylobacterium* that inhibit growth of a plant pathogenic fungus and an agriculturally acceptable excipient and/or an agriculturally acceptable adjuvant. In certain embodiments, the *Methylobacterium* sp. is selected from the group consisting of *M. aminovorans, M. extorquens, M. fujisawaense, M. mesophilicum, M. radiotolerans, M. rhodesianum, M. nodulans, M. phyllosphaerae, M. thiocyanatum*, and *M. oryzae*. In certain embodiments, the *Methylobacterium* is not *M. radiotolerans* or *M. oryzae*. In certain embodiments, the plant pathogenic fungus is selected from the group consisting of an *Alternaria* sp., an *Ascochyta* sp., an *Aspergillus* sp., a *Bipolaris* sp., a *Botrytis* sp., a *Bremia* sp., a *Cercospora* sp., a *Cochliobolus* sp., a *Colletotrichum* sp., a *Diplodia* sp., an *Erysiphe* sp., an *Exserohilum* sp., a *Fusarium* sp., *Gaeumanomyces* sp., *Macrophomina* sp., a *Magnaporthe* sp., a *Nectria* sp., a *Peronospora* sp., a *Phakopsora* sp., a *Phialophora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp, a *Pythium* sp., a *Rhizoctonia* sp., a *Sclerotium* sp., a *Sclerotinia* sp., a *Septoria* sp., a *Stagonospora* sp., a *Thielaviopsis* sp., an *Uncinula* sp, an *Ustilago* sp., a *Venturia* sp., and a *Verticillium* sp. In certain embodiments, the *Fusarium* sp. is selected from the group consisting of *Fusarium graminearum, Fusarium verticillioides, Fusarium oxysporum, Fusarium virguliforme*, and *Fusarium solani*. In certain embodiments of any of the aforementioned compositions, the composition comprises a solid substance wherein a mono-culture or co-culture of *Methylobacterium* is adhered thereto. In certain embodiments, the plant pathogenic fungus is a *Rhizoctonia* sp. or a *Sclerotinia* sp. In certain embodiments, the *Rhizoctonia* sp. is *Rhizoctonia solani* or *Rhizoctonia cerealis*. In certain embodiments, the *Sclerotinia* sp. is *Sclerotinia sclerotiorum* or *Sclerotinia homoeocarpa*. In certain embodiments, the composition comprises a colloid formed by the solid substance wherein a mono-culture or co-culture of *Methylobacterium* is adhered thereto and a liquid. In certain embodiments, the colloid is a gel. In certain embodiments of any of the aforementioned compositions, the composition is an emulsion. In certain embodiments of any of the aforementioned compositions, the *Methylobacterium* is NLS0066 (NRRL B-50940), NLS0089 (NRRL B-50933), a combination of NLS0066 and NLS0017 (NRRL B-50931), or a derivative thereof. In certain embodiments of any of the aforementioned compositions, the composition further comprises *Methylobacterium* strain NLS0020 (NRRL B-50930) or a derivative thereof. In certain embodiments of any of the aforementioned compositions, the *Methylobacterium* is NLS0066, NLS0089, a combination of NLS0066 and NLS0017, a combination of NLS0066 and NLS0020, a combination of NLS0089 and NLS0020, or a derivative thereof. In certain embodiments, the *Methylobacterium* is NLS0089 and the plant pathogenic fungus is a *Rhizoctonia* sp. or a *Sclerotinia* sp. In certain embodiments, the *Methylobacterium* is NLS066, NLS066 and NLS0017, NLS0089, or NLS0089 and NLS0020 and the plant pathogenic fungus is *Fusarium graminearum, Cercospora zeae-maydis*, or *Colletotrichum graminicola*. In certain embodiments, the *Methylobacterium* is NLS0089, or NLS0089 and NLS0020 and the plant pathogenic fungus is *Septoria tritici, Stagonospora nodorum, Pythium* spp., *Rhizoctonia solani*, a *Fusarium* spp., *Magnaportha grisea, Pyrenophora tritici-repentis, Microdochium nivale, Sclerotinia sclerotiorum, Cercospora sojina, Cercospora kikuchii, Fusarium* spp., *Rhizoctonia solani, Fusarium virguliforme, Pythium* spp., *Rhizoctonia solani, Gibberella zeae*, or a *Pythium* spp. In certain embodiments of any of the aforementioned compositions, the *Methylobacterium* sp. that inhibits growth of a plant pathogenic fungus has at least one polymorphic DNA element or orthologous gene that is present in *Methylobacterium* isolate NLS0066 but that is absent from one or more *Methylobacterium* isolates NLS0020 and NLS0037 that do not inhibit *Fusarium graminearum* infections of plants. In certain embodiments, the *Methylobacterium* sp. that inhibits growth of a plant pathogenic fungus has at least one gene that is orthologous to, or that has at least 95%, 97%, 98%, 99%, 99.5%, or 100% sequence identity to, at least one gene selected from the group consisting of SEQ ID NO: 7279-9187, and 9188. In certain embodiments, the *Methylobacterium* sp. that inhibits growth of a plant pathogenic fungus has at least one gene that is orthologous to, or that encodes a protein having at least 95%, 97%, 98%, 99%, 99.5%, or 100% sequence identity to, at least one protein selected from the group consisting of SEQ ID NO: 2585-4593, and 4594. In any of the aforementioned embodiments, the plant pathogen fungus that is inhibited can be in its anamorphic form, its teleomorphic form, or in both its anamorphic form and its teleomorphic forms. In any of the aforementioned embodiments, the composition can comprise a fungal inhibitory concentration of the mono- or co-culture of *Methylobacterium*. In any of the aforementioned embodiments, the composition can further comprise an antifungal compound selected from the group consisting of an azole, dithiocarbamate, strobilurin, and benzimidazole. In certain embodiments, the azole is ipconazole. Use of any of the aforementioned compositions for coating or partially coating a plant part (e.g., a seed) to inhibit growth of any of the aforementioned plant pathogenic fungi is also provided herein.

Also provided are plants or plant parts that are at least partially coated with any of the aforementioned compositions comprising a mono- or co-culture of *Methylobacterium*. In certain embodiments, the at least partially coated plant or plant part is a cereal plant or cereal plant part. In certain embodiments, the at least partially coated cereal plant is selected from the group consisting of a rice, wheat, corn, barley, millet, sorghum, oat, and rye plant. In certain embodiments, the at least partially coated cereal plant part is selected from the group consisting of a rice, wheat, corn, barley, millet, sorghum, oat, and rye plant part. In certain embodiments the at least partially coated plant or plant part is a dicot plant part. In certain embodiments, the dicot plant or plant part is a soybean, peanut, or tomato plant part. In certain embodiments of any of the aforementioned plants or plant parts, the *Methylobacterium* in the composition was obtained from a plant genus, plant species, plant subspecies, or plant cultivar that is distinct from the genus, species, sub-species, or cultivar of the plant or plant part that is coated with the composition. Also provided are processed plant products that comprise a detectable amount of any of the *Methylobacterium* of any of the aforementioned compositions. In certain embodiments, the *Methylobacterium* that is detected was obtained from a plant genus, plant species, plant sub-species, or plant cultivar that is distinct from the genus, species, sub-species, or cultivar used to obtain the processed plant product. In certain embodiments, the *Methylobacterium* is NLS066, NLS066 and NLS0017, NLS0089, or NLS0089 and NLS0020, the plant pathogenic fungus that is inhibited is *Fusarium graminearum* and the plant or plant part is a wheat plant or plant part. In certain embodiments, the *Methylobacterium* is NLS066, NLS066 and NLS0017, NLS0089, or NLS0089 and NLS0020, the plant pathogenic fungus that is inhibited is *Cercospora zeae-maydis*, or *Colletotrichum graminicola*, and the plant or plant part is a corn plant or corn plant part. In certain embodiments, the *Methylobacterium* is NLS0089 or NLS0089 and NLS0020, the plant pathogenic fungus that is inhibited is *Septoria tritici, Stagonospora nodorum, Pythium* spp., *Rhizoctonia solani*, a *Fusarium* spp., *Magnaportha grisea, Pyrenophora tritici-repentis, Microdochium nivale*, and the plant or plant part is a wheat plant or wheat plant part. In certain embodiments, the *Methylobacterium* is NLS0089 or NLS0089 and NLS0020, the plant pathogenic fungus that is inhibited is *Sclerotinia sclerotiorum, Cercospora sojina, Cercospora kikuchii, Fusarium* spp., *Rhizoctonia solani, Fusarium virguliforme, Pythium* spp., and the plant or plant part is a soybean plant or soybean plant part. In certain embodiments, the *Methylobacterium* is NLS0089 or NLS0089 and NLS0020 and the plant pathogenic fungus that is inhibited is a *Fusarium* spp., *Pythium* spp., or *Gibberella zeae*, and the plant or plant part is a corn plant or corn plant part. In certain embodiments, the plant or plant part comprises a fungal inhibitory amount of the *Methylobacterium*. In certain embodiments, a fungal inhibitory amount of the *Methylobacterium* applied to a plant part (e.g., a seed) is about $1.0 \times 10^3$, $1.0 \times 10^4$, or $1.0 \times 10^5$ to about $1.0 \times 10^7$ or $1.0 \times 10^8$ CFUs of PPFM bacteria/plant part (e.g., a seed). In certain embodiments, the *Methylobacterium* is heterologous to the plant or plant part. In certain embodiments of any of the aforementioned plant parts, the plant part is a leaf, a stem, a flower, a root, a tuber, or a seed.

Also provided are methods of making any of the aforementioned compositions containing the *Methylobacterium* that inhibit growth of a plant pathogenic fungus that comprise combining a *Methylobacterium* that inhibit growth of a plant pathogenic fungus with an agriculturally acceptable excipient and/or with an agriculturally acceptable adjuvant. In certain embodiments of the methods, the *Methylobacterium* sp. is selected from the group consisting of *M. aminovorans, M. extorquens, M. fujisawaense, M. mesophilicum, M. radiotolerans, M. rhodesianum, M. nodulans, M. phyllosphaerae, M thiocyanatum*, and *M. oryzae*. In certain embodiments of the methods, the *Methylobacterium* is not *M. radiotolerans* or *M. oryzae*. In certain embodiments of the methods, the *Methylobacterium* is NLS0066, NLS0089, a combination of NLS0066 and NLS0017, or a derivative thereof. In certain embodiments of any of the aforementioned methods, the composition further comprises *Methylobacterium* strain NLS0020 or a derivative thereof. In certain embodiments of any of the aforementioned methods, the *Methylobacterium* is NLS0066, NLS0089, a combination of NLS0066 and NLS0017, a combination of NLS0066 and NLS0020, a combination of NLS0089 and NLS0020, or a derivative thereof. In certain embodiments, the plant or plant part is a soybean plant or soybean plant part. In certain embodiments, the plant or plant part is selected from the group consisting of a rice, wheat, corn, barley, millet, sorghum, oat, and rye plant or plant part. In certain embodiments, the *Methylobacterium* is NLS0089 and the plant pathogenic fungus is a *Rhizoctonia* sp. or a *Sclerotinia* sp. In certain embodiments of the methods, the *Methylobacterium* sp. that inhibit growth of a plant pathogenic fungus has at least one polymorphic DNA element or orthologous gene that is present in NLS0066 but that is absent from one or more *Methylobacterium* isolates NLS0020 and/or NLS0037 that do not inhibit *Fusarium graminearum* infections of plants. In certain embodiments of the methods, the *Methylobacterium* sp. that inhibits growth of a plant pathogenic fungus has at least one gene that is orthologous to, or that has at least 95%, 97%, 98%, 99%, 99.5%, or 100% sequence identity to, at least one gene selected from the group consisting of SEQ ID NO: 7279-9187, and 9188. In certain embodiments of the methods, the *Methylobacterium* sp. that inhibits growth of a plant pathogenic fungus has at least one gene that is orthologous to, or that encodes a protein having at least 95%, 97%, 98%, 99%, 99.5%, or 100% sequence identity to, at least one protein selected from the group consisting of SEQ ID NO: 2585-4593, and 4594. In certain embodiments of the methods, the plant pathogenic fungus is selected from the group consisting of an *Alternaria* sp., an *Ascochyta* sp., an *Aspergillus* sp., a *Bipolaris* sp., a *Botrytis* sp., a *Bremia* sp., a *Cercospora* sp., a *Cochliobolus* sp., a *Colletotrichum* sp., a *Diplodia* sp., an *Erysiphe* sp., an *Exserohilum* sp., a *Fusarium* sp., *Gaeumanomyces* sp., *Macrophomina* sp., a *Magnaporthe* sp., a *Nectria* sp., a *Peronospora* sp., a *Phakopsora* sp., a *Phialophora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp, a *Pythium* sp., a *Rhizoctonia* sp., a *Sclerotium* sp., a *Sclerotinia* sp., a *Septoria* sp., a *Stagonospora* sp., a *Thielaviopsis* sp., an *Uncinula* sp, an *Ustilago* sp., a *Venturia* sp., and a *Verticillium* sp. In certain embodiments of the methods, the plant pathogenic fungus is a *Fusarium* sp. In certain embodiments of the methods, the *Fusarium* sp. is selected from the group consisting of *Fusarium graminearum, Fusarium verticillioides, Fusarium oxysporum, Fusarium virguliforme*, and *Fusarium solani*. In certain embodiments of any of the aforementioned methods, the mono- or co-culture of *Methylobacterium* is adhered to a solid substance. In certain embodiments of the methods, the *Methylobacterium* that is adhered to the solid substance is combined with a liquid to form a composition that is a colloid. In certain embodiments of the methods, the colloid is a gel. In certain embodiments of the methods, the mono- or co-culture of *Methylobacterium* adhered to the solid substance is provided by culturing the *Methylobacterium* in the presence of the solid substance. In certain embodiments of the methods, the composition comprises an emulsion. In certain embodiments of the methods, the *Methylobacterium* is provided by culturing the *Methylobacterium* in an emulsion. In any of the aforementioned embodiments, the plant pathogen fungus that is inhibited can be in its anamorphic form, its teleomorphic form, or in both its anamorphic and teleomorphic forms. In any of the aforementioned embodiments, the composition can further comprise an antifungal compound selected from the group consisting of an azole, dithiocarbamate, strobilurin, and benzimidazole. In certain embodiments, the azole is ipconazole.

Also provided are methods for controlling a plant pathogenic fungus that comprise applying any of the aforementioned compositions that contain a *Methylobacterium* that inhibits growth of a plant pathogenic fungus to a plant or a plant part in an amount that provides for inhibition of infection by the plant pathogenic fungus in the plant, plant part, or a plant obtained therefrom relative to infection of a control plant, plant part, or plant obtained therefrom that had not received an application of the composition. In certain embodiments of the methods, the application of the composition provides for at least 40%, 50%, 75%, at least 85%, or at least 95% inhibition of a plant pathogenic fungal infection in the plant, plant part, or a plant derived therefrom relative to infection of the control plant, plant part, or plant obtained therefrom. In certain embodiments of the methods, the plant part is selected from the group consisting of a leaf, a stem, a flower, a root, a tuber, and a seed. In certain embodiments of the methods, the method further comprises the step of harvesting at least one plant part selected from the group consisting of a leaf, a stem, a flower, a root, a tuber, or a seed from the plant or plant part. In certain embodiments of the methods, the mycotoxin levels in the plant part are reduced by at least 50%, at least 75%, at least 85%, or at least 95% relative to a plant part obtained from the control plant, plant part, or plant obtained therefrom. In certain embodiments of the aforementioned methods, the method further comprises obtaining a processed food or feed composition from the plant or plant part. In certain embodiments of the aforementioned methods, the mycotoxin levels in the processed food or feed composition are reduced by at least 50%, at least 75%, at least 85%, or at least 95% relative to a processed food or feed composition obtained from the control plant, plant part, or plant obtained therefrom. In certain embodiments, a fungal inhibitory amount of the *Methylobacterium* is applied to the plant part. In certain embodiments, the fungal inhibitory amount of the *Methylobacterium* applied to a plant part (e.g., a seed) is about $1.0\times10^3$, $1.0\times10^4$, or $1.0\times10^5$ to about $1.0\times10^7$, $1.0\times10^8$, $1.0\times10^9$, or $1.0\times10^{10}$ CFUs of *Methylobacterium*/plant part (e.g., a seed). In certain embodiments, the *Methylobacterium* is heterologous to the plant or plant part. In certain embodiments of any of the aforementioned methods, the plant part is a leaf, a stem, a flower, a root, a tuber, or a seed. In certain embodiments of the methods, the *Methylobacterium* is NLS0066, NLS0089, a combination of NLS0066 and NLS0017, or a derivative thereof. In certain embodiments of any of the aforementioned methods, the composition further comprises *Methylobacterium* strain NLS0020 or a derivative thereof. In certain embodiments of any of the aforementioned methods, the *Methylobacterium* is NLS0066, NLS0089, a combination of NLS0066 and NLS0017, a combination of NLS0066 and NLS0020, a combination of NLS0089 and NLS0020, or a derivative thereof. In certain embodiments, the plant or plant part is a soybean plant or soybean plant part. In certain embodiments, the plant or plant part is selected from the group consisting of a rice, wheat, corn, barley, millet, sorghum, oat, and rye plant or plant part. In certain embodiments, the *Methylobacterium* is NLS0089 and the plant pathogenic fungus is a *Rhizoctonia* spp. or a *Sclerotinia* spp. In certain embodiments, the *Methylobacterium* is NLS066, NLS066 and NLS0017, NLS0089, or NLS0089 and NLS0020, the plant pathogenic fungus that is inhibited is *Fusarium graminearum* and the plant or plant part is a wheat plant or plant part. In certain embodiments, the *Methylobacterium* is NLS066, NLS066 and NLS0017, NLS0089, or NLS0089 and NLS0020, the plant pathogenic fungus that is inhibited is *Cercospora zeae-maydis*, or *Colletotrichum graminicola*, and the plant or plant part is a corn plant or corn plant part. In certain embodiments, the *Methylobacterium* is NLS0089 or NLS0089 and NLS0020, the plant pathogenic fungus that is inhibited is *Septoria tritici, Stagonospora nodorum, Pythium* spp., *Rhizoctonia solani*, a *Fusarium* spp., *Magnaportha grisea, Pyrenophora tritici-repentis, Microdochium nivale*, and the plant or plant part is a wheat plant or wheat plant part. In certain embodiments, the *Methylobacterium* is NLS0089 or NLS0089 and NLS0020, the plant pathogenic fungus that is inhibited is *Sclerotinia sclerotiorum, Cercospora sojina, Cercospora kikuchii, Fusarium* spp., *Rhizoctonia solani, Fusarium virguliforme, Pythium* spp., and the plant or plant part is a soybean plant or soybean plant part. In certain embodiments, the *Methylobacterium* is NLS0089 or NLS0089 and NLS0020 and the plant pathogenic fungus that is inhibited is a *Fusarium* spp., *Pythium* spp., or *Gibberella zeae*, and the plant or plant part is a corn plant or corn plant part.

Also provided are isolated *Methylobacterium* that inhibit growth of a plant pathogenic fungus. In certain embodiments, the *Methylobacterium* has at least one polymorphic DNA element or orthologous gene that is present in NLS0066 but that is absent from one or more *Methylobacterium* isolates NLS0020 and/or NLS0037 that do not inhibit *Fusarium graminearum* infections of plants. In certain embodiments, the *Methylobacterium* sp. that inhibits growth of a plant pathogenic fungus has at least one gene that is orthologous to, or that has at least 95%, 97%, 98%, 99%, 99.5%, or 100% sequence identity to, at least one gene selected from the group consisting of SEQ ID NO: 7279-9187, and 9188. In certain embodiments, the *Methylobacterium* sp. that inhibits growth of a plant pathogenic fungus has at least one gene that is orthologous to, or that encodes a protein having at least 95%, 97%, 98%, 99%, 99.5%, or 100% sequence identity to, at least one protein selected from the group consisting of SEQ ID NO: 2585-4593, and 4594. In certain embodiments, the *Methylobacterium* is selected from the group consisting of *M. aminovorans, M. extorquens, M. fujisawaense, M. mesophilicum, M. radiotolerans, M. rhodesianum, M. nodulans, M. phyllosphaerae, M. thiocyanatum*, and *M. oryzae*. In certain embodiments, the *Methylobacterium* is not *M. radiotolerans* or *M. oryzae*. In certain embodiments, the plant pathogenic fungus is selected from the group consisting of an *Alternaria* sp., an *Ascochyta* sp., an *Aspergillus* sp., a *Bipolaris* sp., a *Botrytis* sp., a *Bremia* sp., a *Cercospora* sp., a *Cochliobolus* sp., a *Colletotrichum* sp., a *Diplodia* sp., an *Erysiphe* sp., an *Exserohilum* sp., a *Fusarium* sp., *Gaeumanomyces* sp., *Macrophomina* sp., a *Magnaporthe* sp., a *Nectria* sp., a *Peronospora* sp., a *Phakopsora* sp., a *Phialophora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp, a *Pythium* sp., a *Rhizoctonia* sp., a *Sclerotium* sp., a *Sclerotinia* sp., a *Septoria* sp., a *Stagonospora* sp., a *Thielaviopsis* sp., an *Uncinula* sp, an *Ustilago* sp., a *Venturia* sp., and a *Verticillium* sp. In any of the aforementioned embodiments, the plant pathogen fungi that is inhibited can be in its anamorphic form, its teleomorphic form, or in both its anamorphic and teleomorphic forms.

BRIEF DESCRIPTION OF THE DRAWINGS

The accompanying drawings, which are incorporated in and form a part of the specification, illustrate certain embodiments of the present disclosure. In the drawings.

DESCRIPTION

Definitions

Figure 1:
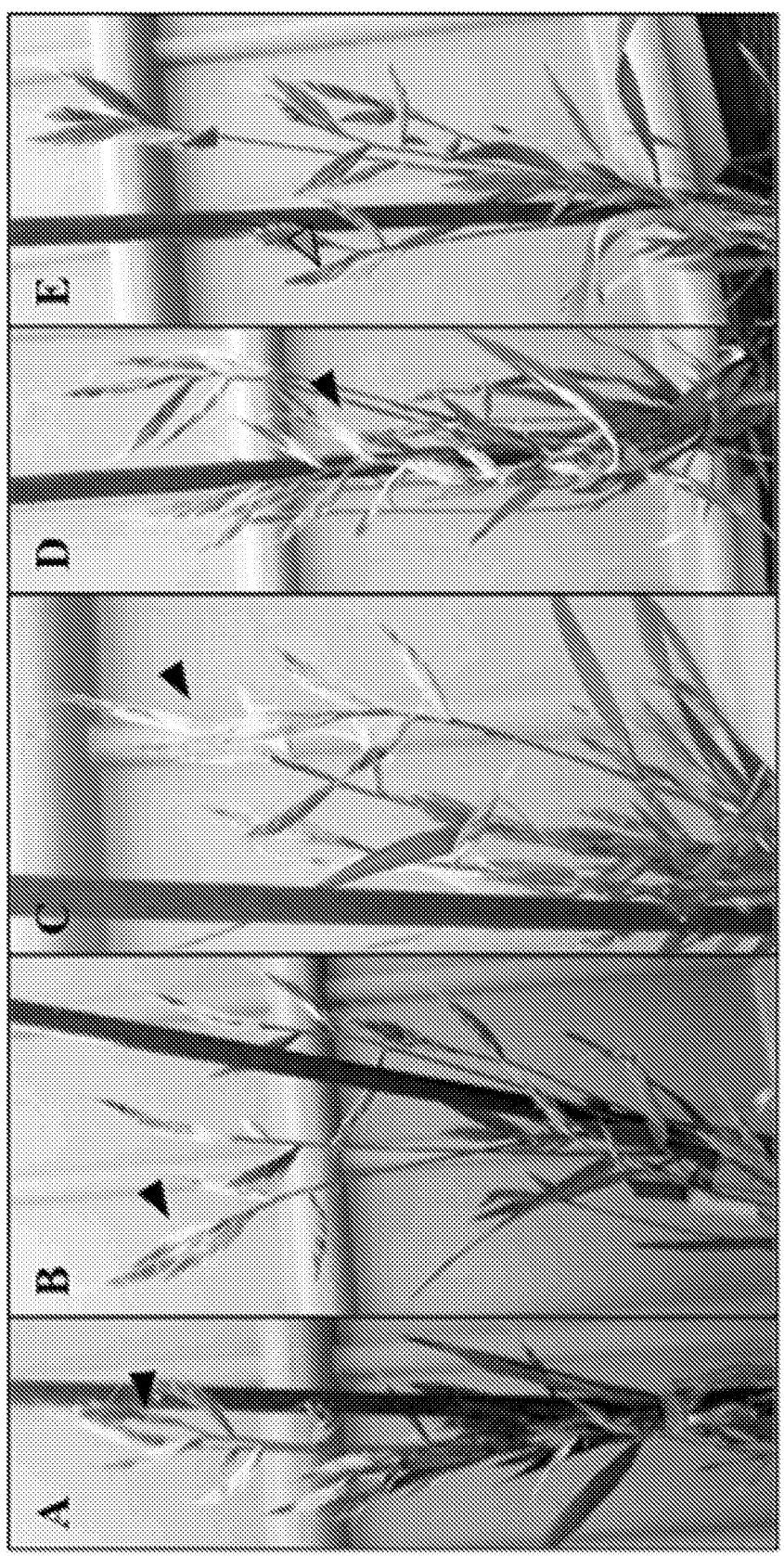
FIG. 1 is a photograph of representative disease outcomes on PPFM-treated *Brachypodium distachyon* plants. Black arrowheads indicate significant disease development, as evidenced by the presence of abundant white fungal mycelia and spikelet necrosis, on plants receiving A) no-PPFM control treatment, B) PPFM strain NLS0017 seed treatment, C) PPFM strain NLS0020 seed treatment and D) PPFM strain NLS0037 seed treatment. Plants receiving E) seed treatment with PPFM strain NLS0066 had significantly reduced spikelet necrosis and abundance of fungal mycelia, as indicated by the grey arrowhead.

As used herein, the phrases "adhered thereto" and "adherent" refer to *Methylobacterium* that are associated with a solid substance by growing, or having been grown, on a solid substance.

As used herein, the phrase "agriculturally acceptable adjuvant" refers to a substance that enhances the performance of an active agent in a composition comprising a mono-culture or co-culture of *Methylobacterium* for treatment of plants and/or plant parts.

As used herein, the phrase "agriculturally acceptable excipient" refers to an essentially inert substance that can be used as a diluent and/or carrier for an active agent in a composition for treatment of plants and/or plant parts. In certain compositions, an active agent can comprise a mono-culture or co-culture of *Methylobacterium*.

As used herein, the phrase "derivatives thereof", when used in the context of a *Methylobacterium* isolate, refers to any strain that is obtained from the *Methylobacterium* isolate. Derivatives of a *Methylobacterium* isolate include, but are not limited to, variants of the strain obtained by selection, variants of the strain selected by mutagenesis and selection, and genetically transformed strains obtained from the *Methylobacterium* isolate.

As used herein, the term "*Methylobacterium*" refers to bacteria that are facultative methylotrophs of the genus *Methylobacterium*. The term *Methylobacterium*, as used herein, thus does not encompass includes species in the genera *Methylobacter, Methylomonas, Methylomicrobium, Methylococcus, Methylosinus, Methylocystis, Methylosphaera, Methylocaldum*, and *Methylocella*, which are obligate methanotrophs.

As used herein, the phrase "co-culture of *Methylobacterium*" refers to a *Methylobacterium* culture comprising at least two strains of *Methylobacterium* or at least two species of *Methylobacterium*.

As used herein, the term "cultivar" refers to any plant known only in cultivation and includes asexually propagated plants, sexually propagated plants, inbred lines, and hybrids.

As used herein, the phrase "contaminating microorganism" refers to microorganisms in a culture, fermentation broth, fermentation broth product, or composition that were not identified prior to introduction into the culture, fermentation broth, fermentation broth product, or composition.

As used herein, the term "emulsion" refers to a colloidal mixture of two immiscible liquids wherein one liquid is the continuous phase and the other liquid is the dispersed phase. In certain embodiments, the continuous phase is an aqueous liquid and the dispersed phase is liquid that is not miscible, or partially miscible, in the aqueous liquid.

As used herein, the phrase "essentially free of contaminating microorganisms" refers to a culture, fermentation broth, fermentation product, or composition where at least about 95% of the microorganisms present by amount or type in the culture, fermentation broth, fermentation product, or composition are the desired *Methylobacterium* or other desired microorganisms of pre-determined identity.

As used herein, the phrase "a fungal inhibitory concentration of the mono- or co-culture of *Methylobacterium*" is a concentration that provides for at least a 40%, 50%, 75%, at least 85%, or at least 95% inhibition of a plant pathogenic fungal infection in a plant, plant part, or a plant derived therefrom relative to infection of the control plant or plant part.

As used herein, the term "heterologous", when used in the context of *Methylobacterium* that at least partially coats a plant or plant part, refers to a *Methylobacterium* that is not naturally associated with a plant or plant part of the same species as the plant or plant part that is at least partially coated with the *Methylobacterium*. In certain embodiments, the heterologous *Methylobacterium* that is used to at least partially coat a plant or plant part of a first plant species is a *Methylobacterium* that was isolated, or can be isolated, from a second and distinct plant species.

As used herein, the phrase "inanimate solid substance" refers to a substance which is insoluble or partially soluble in water or aqueous solutions and which is either non-living or which is not a part of a still-living organism from which it was derived.

As used herein, the phrase "mono-culture of *Methylobacterium*" refers to a *Methylobacterium* culture consisting of a single strain of *Methylobacterium*.

As used herein, a "pesticide" refers to an agent that is insecticidal, fungicidal, nematocidal, bacteriocidal, or any combination thereof.

As used herein, the phrase "bacteriostatic agent" refers to agents that inhibit growth of bacteria but do not kill the bacteria.

As used herein, the phrase "pesticide does not substantially inhibit growth of the *Methylobacterium*" refers to any pesticide that when provided in a composition comprising a fermentation product comprising a solid substance wherein a mono-culture or co-culture of *Methylobacterium* is adhered thereto, results in no more than a 50% inhibition of *Methylobacterium* growth when the composition is applied to a plant or plant part in comparison to a composition lacking the pesticide. In certain embodiments, the pesticide results in no more than a 40%, 20%, 10%, 5%, or 1% inhibition of *Methylobacterium* growth when the composition is applied to a plant or plant part in comparison to a composition lacking the pesticide.

As used herein, the term "PPFM bacteria" refers without limitation to bacterial species in the genus *Methylobacterium* other than *M. nodulans*.

As used herein, the phrase "solid substance" refers to a substance which is insoluble or partially soluble in water or aqueous solutions.

As used herein, the phrase "solid phase that can be suspended therein" refers to a solid substance that can be distributed throughout a liquid by agitation.

As used herein, the term "non-regenerable" refers to either a plant part or processed plant product that cannot be regenerated into a whole plant.

As used herein, the phrase "substantially all of the solid phase is suspended in the liquid phase" refers to media wherein at least 95%, 98%, or 99% of solid substance(s) comprising the solid phase are distributed throughout the liquid by agitation.

As used herein, the phrase "substantially all of the solid phase is not suspended in the liquid phase" refers to media where less than 5%, 2%, or 1% of the solid is in a particulate form that is distributed throughout the media by agitation.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Methylobacterium that Inhibit Plant Pathogenic Fungi, Compositions Comprising Methylobacterium that Inhibit Plant Pathogenic Fungi, Methods of their Use, and Methods of Making Various Methylobacterium that inhibit plant pathogenic fungi, compositions comprising these Methylobacterium, methods of using the compositions to inhibit plant pathogenic fungi, and methods of making the compositions are provided herein. As used herein, inhibition of the growth of a plant pathogenic fungus includes any measurable decrease in fungal growth, where fungal growth includes but is not limited to any measurable decrease in the numbers and/or extent of fungal cells, spores, conidia, or mycelia. As used herein, inhibition of infection by a plant pathogenic fungus and/or inhibition of the growth of a plant pathogenic fungus are also understood to include any measurable decrease in the adverse effects caused by fungal growth in a plant. Adverse effects of fungal growth in a plant include, but are not limited to, any type of plant tissue damage or necrosis, any type of plant yield reduction, any reduction in the value of the crop plant product, and/or production of undesirable fungal metabolites or fungal growth by-products including, but not limited to, mycotoxins. Plant pathogen fungi that are inhibited by the compositions and Methylobacterium provided herein can be in their anamorphic form, their teleomorphic form, or in both their anamorphic and teleomorphic forms.

Methylobacterium and compositions comprising the same that inhibit growth of a plant pathogenic fungus are provided herein. In certain embodiments, the Methylobacterium is selected from the group consisting of M. aminovorans, M. extorquens, M. fujisawaense, M. mesophilicum, M. radiotolerans, M. rhodesianum, M. nodulans, M. phyllosphaerae, M. thiocyanatum, and M. oryzae. In certain embodiments, Methylobacterium is not M. radiotolerans or M. oryzae. In certain embodiments, the Methylobacterium or composition provides for at least about 25%, at least about 40%, at least about 50%, or at least about 75% inhibition of plant pathogenic fungal growth in comparison to a control treatment upon exposure to a plant pathogenic fungus. In certain embodiments, the plant pathogenic fungus that is inhibited is selected from the group consisting of an Alternaria sp., an Ascochyta sp., an Aspergillus sp., a Bipolaris sp., a Botrytis sp., a Bremia sp., a Cercospora sp., a Cochliobolus sp., a Colletotrichum sp., a Diplodia sp., an Erysiphe sp., an Exserohilum sp., a Fusarium sp., Gaeumanomyces sp., a Macrophomina sp., a Magnaporthe sp., a Nectria sp., a Peronospora sp., a Phakopsora sp., a Phialophora sp., a Phoma sp., a Phymatotrichum sp., a Phytophthora sp., a Plasmopara sp., a Puccinia sp., a Podosphaera sp., a Pyrenophora sp., a Pyricularia sp, a Pythium sp., a Rhizoctonia sp., a Sclerotium sp., a Sclerotinia sp., a Septoria sp., a Stagonospora sp., a Thielaviopsis sp., an Uncinula sp, an Ustilago sp., a Venturia sp., and a Verticillium sp. In certain embodiments, the plant pathogenic fungus that is inhibited is a Fusarium sp. In certain embodiments, the Fusarium sp. that is inhibited is selected from the group consisting of Fusarium graminearum, Fusarium verticillioides, Fusarium oxysporum, Fusarium virguliforme, and Fusarium solani. In certain embodiments, the isolated Methylobacterium is NLS0066, NLS0089, a combination of NLS0066 and NLS0017, or a derivative thereof. In certain embodiments, the composition further comprises Methylobacterium strain NLS0020 or a derivative thereof. Plant pathogen fungi that are inhibited by the compositions and Methylobacterium provided herein can be in their anamorphic form, their teleomorphic form, or in both their anamorphic and teleomorphic forms.

Also provided are compositions that comprise Methylobacterium that inhibit growth of a plant pathogenic fungus. In certain embodiments, the compositions further comprise an agriculturally acceptable excipient and/or an agriculturally acceptable adjuvant. In certain embodiments, the Methylobacterium sp. is selected from the group consisting of M. aminovorans, M. extorquens, M. fujisawaense, M. mesophilicum, M. radiotolerans, M. rhodesianum, M. nodulans, M. phyllosphaerae, M. thiocyanatum, and M. oryzae. In certain embodiments, the Methylobacterium is not M. radiotolerans or M. oryzae. In certain embodiments, a the composition provides for at least about 25%, about 50%, or about 75% inhibition of plant pathogenic fungal growth in comparison to a control treatment upon exposure to a plant pathogenic fungus. In certain embodiments, the plant pathogenic fungus that is inhibited is selected from the group consisting of an Alternaria sp., an Ascochyta sp., an Aspergillus sp., a Bipolaris sp., a Botrytis sp., a Bremia sp., a Cercospora sp., a Cochliobolus sp., a Colletotrichum sp., a Diplodia sp., an Erysiphe sp., an Exserohilum sp., a Fusarium sp., Gaeumanomyces sp., a Macrophomina sp., a Magnaporthe sp., a Nectria sp., a Peronospora sp., a Phakopsora sp., a Phialophora sp., a Phoma sp., a Phymatotrichum sp., a Phytophthora sp., a Plasmopara sp., a Puccinia sp., a Podosphaera sp., a Pyrenophora sp., a Pyricularia sp, a Pythium sp., a Rhizoctonia sp., a Sclerotium sp., a Sclerotinia sp., a Septoria sp., a Stagonospora sp., a Thielaviopsis sp., an Uncinula sp, an Ustilago sp., a Venturia sp., and a Verticillium sp. In certain embodiments, the plant pathogenic fungus that is inhibited is a Fusarium sp. In certain embodiments, the Fusarium sp., which is inhibited is selected from the group consisting of Fusarium graminearum, Fusarium verticillioides, Fusarium oxysporum, Fusarium virguliforme, and Fusarium solani. In certain embodiments of any of the aforementioned compositions, the composition comprises a solid substance wherein a mono-culture or co-culture of Methylobacterium is adhered thereto. In certain embodiments where the Methylobacterium is adhered to a solid substance, the composition comprises a colloid formed by the solid substance wherein a mono-culture or co-culture of Methylobacterium is adhered thereto and a liquid. In certain embodiments, the colloid is a gel. In certain embodiments of certain aforementioned compositions, composition is an emulsion that does not contain a solid substance. In certain embodiments of any of the aforementioned compositions, the Methylobacterium has at least one polymorphic DNA element or orthologous gene that is present in NLS0066 but that is absent from one or more Methylobacterium isolates NLS0020 and/or NLS0037 that do not inhibit Fusarium graminearum infections of plants. In certain embodiments of any of the aforementioned compositions, the Methylobacterium sp. that inhibits growth of a plant pathogenic fungus has at least one gene that is orthologous to, or that has at least 95%, 97%, 98%, 99%, 99.5%, or 100% sequence identity to, at least one gene selected from the group consisting of SEQ ID NO: 7279-9187, and 9188. In certain embodiments of any of the aforementioned compositions, the *Methylobacterium* sp. that inhibits growth of a plant pathogenic fungus has at least one gene that is orthologous to, or that encodes a protein having at least 95%, 97%, 98%, 99%, 99.5%, or 100% sequence identity to at least one protein selected from the group consisting of SEQ ID NO: 2585-4593, and 4594. In certain embodiments of any of the aforementioned compositions, the *Methylobacterium* is NLS0066, NLS0089, a combination of NLS0066 and NLS0017, or a derivative thereof. In certain embodiments of any of the aforementioned compositions, the composition further comprises *Methylobacterium* strain NLS0020 or a derivative thereof. In any of the aforementioned embodiments, the plant pathogen fungi that are inhibited can be in their anamorphic form, their teleomorphic form, or in both their anamorphic and teleomorphic forms.

In certain embodiments, the *Methylobacterium* sp. inhibit plant pathogenic fungi can be identified by testing newly isolated candidate *Methylobacterium* sp. for the presence of polymorphic nucleic acid, orthologous gene, or gene sequences that are present in *Methylobacterium* sp. provided herein that inhibit certain plant pathogenic fungi and that are absent from *Methylobacterium* sp. provided herein that do not inhibit *Fusarium graminearum* infections of plants. A candidate *Methylobacterium* sp. has at least one gene that is orthologous to a gene present in *Methylobacterium* sp. that inhibits certain plant pathogenic fungi when a chromosome and/or any extrachromosomal DNA in that candidate *Methylobacterium* sp.: (i) contains a gene encoding a protein that has at least 50%, at least 60%, at least 70%, at least 80%, at least 90%, at least 95%, at least 97%, at least 98%, at least 99%, or 100% sequence identity across the entire length of the amino acid sequence of that protein that is present in the *Methylobacterium* sp. that inhibits certain plant pathogenic fungi; or (ii) contains a gene that has at least 50%, at least 60%, at least 70%, at least 80%, at least 90%, at least 95%, at least 97%, at least 98%, at least 99%, at least 99.5%, or 100% sequence identity across the entire length of the nucleic acid sequence of that gene that is present in the *Methylobacterium* sp. that inhibits certain plant pathogenic fungi. In certain embodiments, the polymorphic nucleic acid, orthologous gene, or gene sequences that are present in the identified *Methylobacterium* sp. that inhibit certain plant pathogenic fungi are also present in the *Methylobacterium* sp. isolate NLS0066 provided herein that inhibit certain plant pathogenic fungi but are absent from one or more of the *Methylobacterium* sp. isolates NLS0020 and/or NLS0037 provided herein that do not inhibit *Fusarium graminearum* infections of plants. In certain embodiments, the polymorphic nucleic acid, orthologous gene, or gene sequences that are present in the identified *Methylobacterium* sp. that inhibit plant pathogenic fungi are present in the *Methylobacterium* sp. isolate NLS0066 but are absent in two of the *Methylobacterium* sp. isolates NLS0020 and NLS0037 that do not inhibit *Fusarium graminearum* infections of plants. In certain embodiments, protein sequences present in NLS0066 that can be useful in identifying *Methylobacterium* that inhibit plant pathogenic fungi include, but are not limited to, SEQ ID NO: 2585-4594. Corresponding gene sequences (i.e. nucleic acid sequences) present in NLS0066 that can be useful in identifying *Methylobacterium* that inhibit plant pathogenic fungi include, but are not limited to, SEQ ID NO: 7279-9188. In certain embodiments, a *Methylobacterium* that inhibits plant pathogenic fungi has at least one gene that is orthologous to, or has at least 95%, 97%, 98%, 99%, 99.5%, or 100% sequence identity to at least one gene selected from the group consisting of SEQ ID NO: 7279-9187, and 9188. In certain embodiments, the *Methylobacterium* that inhibits plant pathogenic fungi has at least one gene that encodes a protein having at least 95%, 97%, 98%, 99%, 99.5%, or 100% sequence identity to at least one protein selected from the group consisting of SEQ ID NO: 2585-4593, and 4594. In certain embodiments, the *Methylobacterium* sp. that inhibits plant pathogenic fungi can also have at least one, two, three, four, six, eight, 10, 15, 20, or 50 genes encoding proteins that are: (i) orthologous to proteins having an amino acid sequence of SEQ ID NO: 2585-4593, and 4594; or that (ii) encode proteins having at least 95%, 97%, 98%, 99%, 99.5%, or 100% sequence identity to a protein selected from the group consisting of SEQ ID NO: 2585-4593, and 4594. In certain embodiments, the *Methylobacterium* sp. that inhibits plant pathogenic fungi can have at least one, two, three, four, six, eight, 10, 15, 20, or 50 genes that are orthologous to, or that have at least 95%, 97%, 98%, 99%, 99.5%, or 100% sequence identity to, one or more gene(s) selected from the group consisting of SEQ ID NO: 7279-9187, and 9188.

Such nucleic acid polymorphisms that occur in the *Methylobacterium* sp. that inhibit plant pathogenic fungi can include, but are not limited to, single nucleotide polymorphisms, RFLP, AFLP and/or other DNA variations such as repetitive sequences, insertion sequences, transposons, and genomic islands occurring as a result of insertions, deletions, and substitutions (Indels) in the bacterial genome which includes both the chromosomal DNA as well as any extrachromosomal nucleic acid elements that can be present in the *Methylobacterium* sp. that inhibit plant pathogenic fungi. Such extrachromosomal nucleic acid elements include, but are not limited to, plasmids, bacteriophage DNA or RNA, and the like. Methods used to identify such nucleotide polymorphisms include, but are not limited to, single base extension (SBE) techniques, allele specific hybridization (ASH), real-time PCR detection (i.e. TaqMan™; U.S. Pat. Nos. 5,804,375; 5,538,848; 5,487,972; and 5,210,015, which are each incorporated herein by reference in their entireties), combinations of ASH and RT-PCR (KASP™ detection systems, LGC Genomics, Middlesex, UK) and deep sequencing techniques (U.S. Patent Appl. No. 20120264632, incorporated herein by reference in its entirety).

A *Methylobacterium* sp. can be determined to contain a gene encoding a protein that is orthologous to a protein that is present in a *Methylobacterium* sp. that inhibits plant pathogenic fungi but absent from one or more of the *Methylobacterium* sp. isolates by a variety of different techniques. In certain embodiments, a *Methylobacterium* sp. can be determined to contain a gene encoding a protein that is orthologous to a protein that is present in NLS0066 but absent from one or more of the *Methylobacterium* sp. isolates NLS0020 and/or NLS0037 or that is orthologous to a protein present in NLS0066. In certain embodiments, a *Methylobacterium* sp. can be determined to contain a gene encoding a protein that is orthologous to such proteins by assembling a complete electronic genomic sequence comprising chromosomal and extrachromosomal DNA sequences present in that *Methylobacterium* sp. with a computer and associated software, and determining if any of the open reading frames (ORF) present in that DNA sequence encode a protein having the aforementioned percent sequence identity. In certain embodiments, the ORF can be identified by performing a six-way translation of the electronically assembled sequence and querying the translated sequences with a protein sequence that is present in NLS0066 but absent from one or more of the *Methylobacterium* sp. isolates NLS0020 and/or NLS0037 or with an amino acid sequence of SEQ ID NO: 2585-4594. In other embodiments, the presence or absence of a given sequence within a *Methylobacterium* sp. can be determined by a nucleic acid analysis or protein analysis technique. Examples of nucleic acid sequences that encode the proteins of SEQ ID NO: 2585-4594 include, but are not limited to, SEQ ID NO: 7279-9188 respectively. Such nucleic acid analyses include, but are not limited to, techniques based on nucleic acid hybridization, polymerase chain reactions, mass spectroscopy, nanopore based detection, branched DNA analyses, combinations thereof, and the like. Protein analysis techniques include, but are not limited to, immunodetection, mass spectroscopy, combinations thereof, and the like.

Protein and gene sequences found in the *Methylobacterium* isolate NLS0017 are also provided herewith as SEQ ID NO: 1-2584 and 4595-7278, respectively. *Methylobacterium* isolate NLS0017 has been deposited as NRRL B-50931 with the AGRICULTURAL RESEARCH SERVICE CULTURE COLLECTION (NRRL) of the National Center for Agricultural Utilization Research, Agricultural Research Service, U.S. Department of Agriculture, 1815 North University Street, Peoria, Ill. 61604 U.S.A. under the terms of the Budapest Treaty on the International Recognition of the Deposit of Microorganisms for the Purposes of Patent Procedure). The identification of SEQ ID NO: 1-9188 is described in the co-assigned International Patent Application PCT/US2014/068611, which is incorporated herein by reference in its entirety. Various *Methylobacterium* sp. isolates provided herein are disclosed in Table 1.

TABLE 1

*Methylobacterium* sp. isolates

| NLS | Inhibition of *Fusarium graminearum* | Origin | USDA ARS NRRL No.[1] |
|---|---|---|---|
| NLS0017 | –[2] | Obtained from a peppermint plant grown in Saint Louis County, Missouri, USA | NRRL B-50931 |
| NLS0020 | – | Obtained from a horse nettle plant grown in Saint Louis County, Missouri, USA | NRRL B-50930 |
| NLS0037 | – | Obtained from a tomato plant (cultivar "Champion") grown in Saint Louis County, Missouri, USA | NRRL B-50941 |
| NLS0066 | + | Obtained from the corn hybrid "MC534" (Masters Choice 3010 State Route 146 East Anna, IL 62906) | NRRL B-50940 |
| NLS0089 | + | Obtained from a broccoli plant grown in Saint Louis County, Missouri, USA | NRRL B-50933 |

[1]Deposit number for strain deposited with the AGRICULTURAL RESEARCH SERVICE CULTURE COLLECTION (NRRL) of the National Center for Agricultural Utilization Research, Agricultural Research Service, U.S. Department of Agriculture, 1815 North University Street, Peoria, Illinois 61604 U.S.A. under the terms of the Budapest Treaty on the International Recognition of the Deposit of Microorganisms for the Purposes of Patent Procedure. Subject to 37 CFR §1.808(b), all restrictions imposed by the depositor on the availability to the public of the deposited material will be irrevocably removed upon the granting of any patent from this patent application.
[2]Can improve activity of NLS0066 in a combined NLS0066 + NLS0017 treatment in comparison to NLS0066 alone.

Also provided herein are methods for controlling a plant pathogenic fungus that comprise applying any of the aforementioned compositions comprising the *Methylobacterium* that are provided herein to a plant or a plant part in an amount that provides for inhibition of infection by the plant pathogenic fungus in the plant, plant part, or a plant obtained therefrom relative to infection of a control plant, plant part, or plant obtained therefrom that had not received an application of the composition. In certain embodiments, application of the composition provides for at least about 40%, at least about 50%, at least about 75%, at least about 85%, or at least about 95% inhibition of a plant pathogenic fungal infection in the plant, plant part, or a plant derived therefrom relative to infection of the control plant, plant part, or plant obtained therefrom. In certain embodiments, the plant part is selected from the group consisting of a leaf, a stem, a flower, a root, a tuber, and a seed. In certain embodiments, the method further comprises the step of harvesting at least one plant part selected from the group consisting of a leaf, a stem, a flower, a root, a tuber, or a seed from the plant or plant part. In certain embodiments of any of the aforementioned methods, the mycotoxin levels in the plant part are reduced by at least 50%, at least 75%, at least 85%, or at least 95% relative to a plant part obtained from the control plant, plant part, or plant obtained therefrom. In certain embodiments of any of the aforementioned methods, the methods further comprise obtaining a processed food or feed composition from the plant or plant part. In certain embodiments of the aforementioned methods, mycotoxin levels in the processed food or feed composition are reduced by at least 50%, at least 75%, at least 85%, or at least 95% relative to a processed food or feed composition obtained from the control plant, plant part, or plant obtained therefrom. In certain embodiments of any of the aforementioned methods, the composition comprises a *Methylobacterium* that has at least one polymorphic DNA element, orthologous gene, or gene that is present in NLS0066 but that is absent from one or more *Methylobacterium* isolates NLS0020 and/or NLS0037 that do not inhibit *Fusarium graminearum* infections of plants. In certain embodiments of any of the aforementioned methods, the composition comprises the *Methylobacterium* isolate NLS0066, NLS0089, a combination of NLS0066 and NLS0017, or a derivative thereof. In certain embodiments of any of the aforementioned methods, the composition further comprises *Methylobacterium* strain NLS0020 or a derivative thereof. In certain embodiments of any of the aforementioned methods, the composition comprises a *Methylobacterium* sp. that has at least one gene that is orthologous to, or that has at least 95%, 97%, 98%, 99%, 99.5%, or 100% sequence identity to, at least one gene selected from the group consisting of SEQ ID NO: 7279-9187, and 9188. In certain embodiments of any of the aforementioned methods, the composition comprises a *Methylobacterium* sp. that has at least one gene that that is orthologous to, or that encodes a protein having at least 95%, 97%, 98%, 99%, 99.5%, or 100% sequence identity to, at least one protein selected from the group consisting of SEQ ID NO: 2585-4593, and 4594.

Also provided are methods of making the compositions useful for controlling plant pathogenic fungi that comprise combining a *Methylobacterium* that inhibit growth of a plant pathogenic fungus with an agriculturally acceptable excipient and/or with an agriculturally acceptable adjuvant. In certain embodiments of the methods, the *Methylobacterium* sp. is selected from the group consisting of *M. aminovorans, M. extorquens, M. fujisawaense, M. mesophilicum, M. radiotolerans, M. rhodesianum, M. nodulans, M. phyl-*

*losphaerae, M thiocyanatum*, and *M. oryzae*. In certain embodiments of the methods, the *Methylobacterium* is not *M. radiotolerans* or *M. oryzae*. In certain embodiments of the methods, the *Methylobacterium* that has at least one polymorphic DNA element that is present in NLS0066 but that is absent from one or more *Methylobacterium* isolates NLS0020 and/or NLS0037 that do not inhibit *Fusarium graminearum* infections of plants. In certain embodiments of any of the aforementioned methods, the composition comprises a *Methylobacterium* sp. that has at least one gene that is orthologous to, or that has at least 95%, 97%, 98%, 99%, 99.5%, or 100% sequence identity to, at least one gene selected from the group consisting of SEQ ID NO: 7279-9187, and 9188. In certain embodiments of any of the aforementioned methods, the composition comprises a *Methylobacterium* sp. that has at least one gene that that is orthologous to, or that encodes a protein having at least 95%, 97%, 98%, 99%, 99.5%, or 100% sequence identity to, at least one protein selected from the group consisting of SEQ ID NO: 2585-4593, and 4594. In certain embodiments of any of the aforementioned methods, the composition comprises the *Methylobacterium* isolate NLS0066, NLS0089, a combination of NLS0066 and NLS0017, or a derivative thereof. In certain embodiments of any of the aforementioned methods, the composition further comprises *Methylobacterium* strain NLS0020 or a derivative thereof. In certain embodiments of the methods, the compositions provide for at least about 25%, at least about 50%, or at least about 75% inhibition of plant pathogenic fungal growth in comparison to a control composition that lacks *Methylobacterium* that inhibit a plant pathogenic fungus upon exposure to the plant pathogenic fungus. In certain embodiments of the methods, the plant pathogenic fungus is selected from the group consisting of an *Alternaria* sp., an *Ascochyta* sp., an *Aspergillus* sp., a *Bipolaris* sp., a *Botrytis* sp., a *Bremia* sp., a *Cercospora* sp., a *Cochliobolus* sp., a *Colletotrichum* sp., a *Diplodia* sp., an *Erysiphe* sp., an *Exserohilum* sp., a *Fusarium* sp., *Gaeumanomyces* sp., a *Macrophomina* sp., a *Magnaporthe* sp., a *Nectria* sp., a *Peronospora* sp., a *Phakopsora* sp., a *Phialophora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp, a *Pythium* sp., a *Rhizoctonia* sp., a *Sclerotium* sp., a *Sclerotinia* sp., a *Septoria* sp., a *Stagonospora* sp., a *Thielaviopsis* sp., an *Uncinula* sp, an *Ustilago* sp., a *Venturia* sp., and a *Verticillium* sp. In certain embodiments of the methods, the *Fusarium* sp. is selected from the group consisting of *Fusarium graminearum, Fusarium verticillioides, Fusarium oxysporum*, and *Fusarium solani*. In certain embodiments of the methods, the *Methylobacterium* is adhered to a solid substance. In certain embodiments of the methods, the *Methylobacterium* adhered to the solid substance is combined with a liquid to form a composition that is a colloid. In certain embodiments of the methods, the colloid is a gel. In certain embodiments of the methods, the *Methylobacterium* adhered to the solid substance is provided by culturing the *Methylobacterium* in the presence of the solid substance. In certain embodiments of the methods, the composition comprises an emulsion. In certain embodiments of the methods, the *Methylobacterium* is provided by culturing the *Methylobacterium* in an emulsion. In certain embodiments of any of the aforementioned methods, the plant pathogenic fungus is a *Fusarium* sp. and/or the plant is a cereal plant. In certain embodiments of any of the aforementioned methods, the plant pathogenic fungus is a *Fusarium* sp. and the plant is a cereal plant selected from the group consisting of a rice, wheat, corn, barley, millet, sorghum, oat, and rye plant. In certain embodiments of any of the aforementioned methods, the plant pathogenic fungus is *Fusarium graminearum* and the plant is a cereal plant selected from the group consisting of a rice, wheat, corn, barley, millet, sorghum, oat, and rye plant. In any of the aforementioned embodiments, the plant pathogen fungi that is inhibited can be in its anamorphic form, its teleomorphic form, or in both its anamorphic and teleomorphic forms.

Methods where *Methylobacterium* are cultured in biphasic media comprising a liquid phase and a solid substance have been found to significantly increase the resultant yield of *Methylobacterium* relative to methods where the *Methylobacterium* are cultured in liquid media alone. In certain embodiments, the methods can comprise growing the *Methylobacterium* in liquid media with a particulate solid substance that can be suspended in the liquid by agitation under conditions that provide for *Methylobacterium* growth. In certain embodiments where particulate solid substances are used, at least substantially all of the solid phase can thus be suspended in the liquid phase upon agitation. Such particulate solid substances can comprise materials that are about 1 millimeter or less in length or diameter. In certain embodiments, the degree of agitation is sufficient to provide for uniform distribution of the particulate solid substance in the liquid phase and/or optimal levels of culture aeration. However, in other embodiments provided herein, at least substantially all of the solid phase is not suspended in the liquid phase, or portions of the solid phase are suspended in the liquid phase and portions of the solid phase are not suspended in the liquid phase. Non-particulate solid substances can be used in certain biphasic media where the solid phase is not suspended in the liquid phase. Such non-particulate solid substances include, but are not limited to, materials that are greater than about 1 millimeter in length or diameter. Such particulate and non-particulate solid substances also include, but are not limited to, materials that are porous, fibrous, or otherwise configured to provide for increased surface areas for adherent growth of the *Methylobacterium*. Biphasic media where portions of the solid phase are suspended in the liquid phase and portions of the solid phase are not suspended in the liquid phase can comprise a mixture of particulate and non-particulate solid substances. Such particulate and non-particulate solid substances used in any of the aforementioned biphasic media also include, but are not limited to, materials that are porous, fibrous, or otherwise configured to provide for increased surface areas for adherent growth of the *Methylobacterium*. In certain embodiments, the media comprises a colloid formed by a solid and a liquid phase. A colloid comprising a solid and a liquid can be pre-formed and added to liquid media or can be formed in media containing a solid and a liquid. Colloids comprising a solid and a liquid can be formed by subjecting certain solid substances to a chemical and/or thermal change. In certain embodiments, the colloid is a gel. In certain embodiments, the liquid phase of the media is an emulsion. In certain embodiments, the emulsion comprises an aqueous liquid and a liquid that is not miscible, or only partially miscible, in the aqueous liquid. Liquids that are not miscible, or only partially miscible, in water include, but are not limited to, any of the following: (1) liquids having a miscibility in water that is equal to or less than that of pentanol, hexanol, or heptanol at 25 degrees C.; (2) liquids comprising an alcohol, an aldehyde, a ketone, a fatty acid, a phospholipid, or any combination thereof; (3) alcohols selected from the group consisting of aliphatic alcohols containing at least 5 carbons and sterols; (4) an animal oil, microbial oil, synthetic oil, plant oil, or combination thereof; and/or, (5) a plant oil selected from the group consisting of corn, soybean, cotton, peanut, sunflower, olive, flax, coconut, palm, rapeseed, sesame seed, safflower, and combinations thereof. In certain embodiments, the immiscible or partially immiscible liquid can comprises at least about 0.02% to about 20% of the liquid phase by mass. In certain embodiments, the methods can comprise obtaining a biphasic culture media comprising the liquid, the solid, and *Methylobacterium* and incubating the culture under conditions that provide for growth of the *Methylobacterium*. Biphasic culture medias comprising the liquid, the solid, and *Methylobacterium* can be obtained by a variety of methods that include, but are not limited to, any of: (a) inoculating a biphasic media comprising the liquid and the solid substance with *Methylobacterium*; (b) inoculating the solid substance with *Methylobacterium* and then introducing the solid substance comprising the *Methylobacterium* into the liquid media; (c) inoculating the solid substance with *Methylobacterium*, incubating the *Methylobacterium* on the solid substance, and then introducing the solid substance comprising the *Methylobacterium* into the liquid media; or (d) any combination of (a), (b), or (c). Methods and compositions for growing *Methylobacterium* in biphasic media comprising a liquid and a solid are disclosed in co-assigned U.S. patent application Ser. No. 13/907,161, filed May 31, 2013, which is incorporated herein by reference in its entirety, and in co-assigned International Patent Application PCT/US13/43722, filed May 31, 2013, which is incorporated herein by reference in its entirety.

Methods where *Methylobacterium* are cultured in media comprising an emulsion have also been found to significantly increase the resultant yield of *Methylobacterium* relative to methods where the *Methylobacterium* are cultured in liquid media alone. In certain embodiments, the methods for making the compositions provided herein can comprise growing the *Methylobacterium* in an emulsion under conditions that provide for *Methylobacterium* growth. Medias comprising the emulsion and *Methylobacterium* can be obtained by a variety of methods that include, but are not limited to, any of: (a) inoculating a media comprising the emulsion with *Methylobacterium*; (b) inoculating the aqueous liquid with the *Methylobacterium*, introducing the non-aqueous liquid, and mixing to form an emulsion; (c) inoculating the aqueous liquid with the *Methylobacterium*, introducing the non-aqueous liquid, and mixing to form an emulsion; or (d) any combination of (a), (b), or (c). In certain embodiments, the emulsion comprises an aqueous liquid and a liquid that is not miscible, or only partially miscible, in the aqueous liquid. Non-aqueous liquids that are not miscible, or only partially miscible, in water include, but are not limited to, any of the following: (1) liquids having a miscibility in water that is equal to or less than that of n-pentanol, n-hexanol, or n-heptanol at 25 degrees C.; (2) liquids comprising an alcohol, an aldehyde, a ketone, a fatty acid, a phospholipid, or any combination thereof; (3) alcohols selected from the group consisting of aliphatic alcohols containing at least 5, 6, or 7 carbons and sterols; (4) an animal oil, microbial oil, synthetic oil, plant oil, or combination thereof, and/or, (5) a plant oil selected from the group consisting of corn, soybean, cotton, peanut, sunflower, olive, flax, coconut, palm, rapeseed, sesame seed, safflower, and combinations thereof. In certain embodiments, the immiscible or partially immiscible non-aqueous liquid can comprise at least about 0.02% to about 20% of the emulsion by mass. In certain embodiments, the immiscible or partially immiscible non-aqueous liquid can comprise at least about any of about 0.05%, 0.1%, 0.5%, or 1% to about 3%, 5%, 10%, or 20% of the emulsion by mass. Methods and compositions for growing *Methylobacterium* in media comprising an emulsion are disclosed in co-assigned U.S. Provisional Patent Application No. 61/829,987, filed May 31, 2013, and in co-assigned PCT Application No. PCT/US14/40218, filed May 30, 2014, which are both incorporated herein by reference in their entireties.

In certain embodiments, the fermentation broth, fermentation broth product, or compositions that comprise *Methylobacterium* that inhibit plant pathogenic fungi can further comprise one or more introduced microorganisms of predetermined identity other than *Methylobacterium*. Other microorganisms that can be added include, but are not limited to, microorganisms that are biopesticidal or provide some other benefit when applied to a plant or plant part. Biopesticidal or otherwise beneficial microorganisms thus include, but are not limited to, various *Bacillus* sp., *Pseudomonas* sp., *Coniothyrium* sp., *Pantoea* sp., *Streptomyces* sp., and *Trichoderma* sp. Microbial biopesticides can be a bacterium, fungus, virus, or protozoan. Particularly useful biopesticidal microorganisms include various *Bacillus subtilis, Bacillus thuringiensis, Bacillus pumilis, Pseudomonas syringae, Trichoderma harzianum, Trichoderma virens*, and *Streptomyces lydicus* strains. Other microorganisms that are added can be genetically engineered or isolates that are available as pure cultures. In certain embodiments, it is anticipated that the bacterial or fungal microorganism can be provided in the fermentation broth, fermentation broth product, or composition in the form of a spore.

In certain embodiments, the liquid culture medium is prepared from inexpensive and readily available components, including, but not limited to, inorganic salts such as potassium phosphate, magnesium sulfate and the like, carbon sources such as glycerol, methanol, glutamic acid, aspartic acid, succinic acid and the like, and amino acid blends such as peptone, tryptone, and the like. Examples of liquid media that can be used include, but are not limited to, ammonium mineral salts (AMS) medium (Whittenbury et al., 1970), Vogel-Bonner (VB) minimal culture medium (Vogel and Bonner, 1956), and LB broth ("Luria-Bertani Broth").

In general, the solid substance used in the methods and compositions that provide for the efficient growth of *Methylobacterium* can be any suitable solid substance which is insoluble or only partially soluble in water or aqueous solutions. Such suitable solid substances are also non-bacteriocidal or non-bacteriostatic with respect to *Methylobacterium* that inhibit plant pathogenic fungi when the solid substances are provided in the liquid culture media. In certain embodiments, such suitable solid substances are also solid substances that are readily obtained in sterile form or rendered sterile. Solid substances used herein can be sterilized by any method that provides for removal of contaminating microorganisms and thus include, but are not limited to, methods such as autoclaving, irradiation, chemical treatment, and any combination thereof. These solid substances include substances of animal, plant, microbial, fungal, or mineral origin, manmade substances, or combinations thereof. In certain embodiments, the solid substances are inanimate solid substances. Inanimate solid substances of animal, plant, microbial, or fungal origin can be obtained from animals, plants, microbes, or fungi that are inviable (i.e. no longer living) or that have been rendered inviable. Diatom shells are thus inanimate solid substances when previously associated diatom algae have been removed or otherwise rendered inviable. Since diatom shells are inanimate solid substances, they are not considered to be photosynthetic organisms or photosynthetic microorganisms. In certain embodiments, solid substances include, but are not limited to, sand, silt, soil, clay, ash, charcoal, diatomaceous earth and other similar minerals, ground glass or glass beads, ground ceramic materials, ceramic beads, bentonite, kaolin, talc, perlite, mica, vermiculite, silicas, quartz powder, montmorillonite, and combinations thereof. In certain embodiments, the solid substance can be a polymer or polymeric beads. Polymers that can be used as a solid substance include, but are not limited to, various polysaccharides such as cellulosic polymers and chitinous polymers which are insoluble or only partially soluble in water or aqueous solutions, agar (i.e. galactans), and combinations thereof. In certain embodiments, the solid substance can be an insoluble or only partially soluble salt crystal. Salt crystals that can be used include, but are not limited to, insoluble or only partially soluble carbonates, chromates, sulfites, phosphates, hydroxides, oxides, and sulfides. In certain embodiments, the solid substance can be a microbial cell, fungal cell, microbial spore, or fungal spore. In certain embodiments, the solid substance can be a microbial cell or microbial spore wherein the microbial cell or microbial spore is not a photosynthetic microorganism. In certain embodiments, the microbial cell or microbial spore is not a photosynthetic microorganism, where the photosynthetic microorganism is selected from the group consisting of algae, cyanobacteria, diatoms, *Botryococcus braunii, Chlorella, Dunaliella tertiolecta, Gracilaria, Pleurochrysis carterae, Sargassum*, and *Ulva*. In still other embodiments, the solid substance can be an inactivated (i.e. inviable) microbial cell, fungal cell, microbial spore, or fungal spore. In still other embodiments, the solid substance can be a quiescent (i.e. viable but not actively dividing) microbial cell, fungal cell, microbial spore, or fungal spore. In still other embodiments, the solid substance can be cellular debris of microbial origin. In still other embodiments, the solid substance can be particulate matter from any part of a plant. Plant parts that can be used to obtain the solid substance include, but are not limited to, cobs, husks, hulls, leaves, roots, flowers, stems, bark, seeds, and combinations thereof. Products obtained from processed plant parts including, but not limited to, bagasse, wheat bran, soy grits, crushed seed cake, stover, and the like can also be used. Such plant parts, processed plants, and/or processed plant parts can be milled to obtain the solid material in a particulate form that can be used. In certain embodiments, wood or a wood product including, but not limited to, wood pulp, sawdust, shavings, and the like can be used. In certain embodiments, the solid substance can be a particulate matter from an animal(s), including, but not limited to, bone meal, gelatin, ground or powdered shells, hair, macerated hide, and the like.

In certain embodiments, the solid substance is provided in a particulate form that provides for distribution of the solid substance in the culture media. In certain embodiments, the solid substance is comprised of particle of about 2 microns to about 1000 microns in average length or average diameter. In certain embodiments, the solid substance is comprised of particle of about 1 microns to about 1000 microns in average length or average diameter. In certain embodiments, the solid substance is a particle of about 1, 2, 4, 10, 20, or 40 microns to any of about 100, 200, 500, 750, or 1000 microns in average length or average diameter. Desirable characteristics of particles used in the methods and compositions provided herein include suitable wettability such that the particles can be suspended throughout the media upon agitation.

In certain embodiments, the solid substance is provided in the media as a colloid wherein the continuous phase is a liquid and the dispersed phase is the solid. Suitable solids that can be used to form colloids in liquid media used to grow *Methylobacterium* that inhibit plant pathogenic fungi include, but are not limited to, various solids that are referred to as hydrocolloids. Such hydrocolloids used in the media, methods and compositions provided herein can be hydrophilic polymers, of plant, animal, microbial, or synthetic origin. Hydrocolloid polymers used in the methods can contain many hydroxyl groups and/or can be polyelectrolytes. Hydrocolloid polymers used in the compositions and methods provided herein include, but are not limited to, agar, alginate, arabinoxylan, carrageenan, carboxymethylcellulose, cellulose, curdlan, gelatin, gellan, β-glucan, guar gum, gum arabic, locust bean gum, pectin, starch, xanthan gum, and mixtures thereof. In certain embodiments, the colloid used in the media, methods, and compositions provided herein can comprise a hydrocolloid polymer and one or more proteins.

In certain embodiments, the solid substance can be a solid substance that provides for adherent growth of the *Methylobacterium* that inhibit plant pathogenic fungi on the solid substance. *Methylobacterium* that inhibit plant pathogenic fungi that are adhered to a solid substance are *Methylobacterium* that cannot be substantially removed by simply washing the solid substance with the adherent *Methylobacterium* that inhibit plant pathogenic fungi with growth media whereas non-adherent *Methylobacterium* can be substantially removed by washing the solid substance with liquid growth media. In this context, "substantially removed" means that at least about 30%, 40%, 50%, 60%, 70%, or 80% the *Methylobacterium* present are removed when the solid substance is washed with three volumes of liquid growth media. Such washing can be effected by a variety of methods including, but not limited to, decanting liquid from a washed solid phase or passing liquid through a solid phase on a filter that permits flow through of bacteria in the liquid. In certain embodiments, the adherent *Methylobacterium* that inhibit plant pathogenic fungi that are associated with the solid can include both *Methylobacterium* that are directly attached to the solid and/or *Methylobacterium* that are indirectly attached to the solid substance. *Methylobacterium* that are indirectly attached to the solid substance include, but are not limited to, *Methylobacterium* that are attached to another *Methylobacterium* or to another microorganism that is attached to the solid substance, *Methylobacterium* that are attached to the solid substance by being attached to another substance that is attached to the solid substance, and the like. In certain embodiments, at least 10%, 20%, 30%, 40%, 50%, 60%, 70%, 80%, 90%, 95%, 98%, 99%, 99.5% or 99.9% of the *Methylobacterium* in the fermentation broth, fermentation broth product, or compositions are *Methylobacterium* that are adhered to the solid substance. In certain embodiments, adherent *Methylobacterium* that inhibit plant pathogenic fungi can be present on the surface of the solid substance in the fermentation broth, fermentation broth product, or composition at a density of at least about 1 *Methylobacterium*/20 square micrometers, of at least about 1 *Methylobacterium*/10 square micrometers, of at least about 3 *Methylobacterium*/10 square micrometers, of at least about 1 *Methylobacterium*/5 square micrometers, of at least about 1 *Methylobacterium*/2 square micrometers, or of at least about 1 *Methylobacterium*/square micrometer. In certain embodiments, adherent *Methylobacterium* that inhibit plant pathogenic fungi can be present on the surface of the solid substance in the fermentation broth, fermentation broth product, or composition at a density of at least about 1 *Methylobacterium*/20 square micrometers to about 1 *Methylobacterium*/square micrometer, of at least about 1 *Methylobacterium*/10 square micrometers to about 1 *Methylobacterium*/square micrometer, of at least about 1 *Methylobacterium*/10 square micrometers to about 1 *Methylobacterium*/square micrometer, of at least about 1 *Methylobacterium*/5 square micrometers to about 1 *Methylobacterium*/square micrometer, or of at least about 1 *Methylobacterium*/2 square micrometers to about 1 *Methylobacterium*/square micrometer. In certain embodiments, adherent *Methylobacterium* that inhibit plant pathogenic fungi can be present on the surface of the solid substance in the fermentation broth, fermentation broth product, or composition at a density of at least about 1 *Methylobacterium*/20 square micrometers to about 1 *Methylobacterium*/2 square micrometers, of at least about 1 *Methylobacterium*/10 square micrometers to about 1 *Methylobacterium*/2 square micrometers, of at least about 1 *Methylobacterium*/10 square micrometers to about 1 *Methylobacterium*/2 square micrometers, or of at least about 1 *Methylobacterium*/5 square micrometers to about 1 *Methylobacterium*/2 square micrometers. Biphasic fermentation broths provided herein can comprise a liquid phase that contains non-adherent *Methylobacterium*. In certain embodiments, titers of non-adherent *Methylobacterium* in the liquid phase can be less than about 100,000, 10,000, or 1,000 CFU/ml.

Fermentation products and compositions with a mono- or co-culture of *Methylobacterium* that inhibit plant pathogenic fungi at a titer of greater than about $5 \times 10^7$ colony-forming units per milliliter, at a titer of greater than about $1 \times 10^8$ colony-forming units per milliliter, at a titer of greater than about $5 \times 10^8$ colony-forming units per milliliter, at a titer of greater than about $1 \times 10^9$ colony-forming units per milliliter, at a titer of greater than about $1 \times 10^{10}$ colony-forming units per milliliter, at a titer of at least about $3 \times 10^{10}$ colony-forming units per milliliter are provided herein. In certain embodiments, fermentation products and compositions provided herein can comprise *Methylobacterium* that inhibit plant pathogenic fungi at a titer of at least about $5 \times 10^7$, $1 \times 10^8$, or $5 \times 10^8$ colony-forming units per milliliter to at least about $3 \times 10^{10}$ colony-forming units per milliliter, at least about $5 \times 10^8$ colony-forming units per milliliter to at least about $4 \times 10^{10}$ colony-forming units per milliliter, or at least about $5 \times 10^9$ colony-forming units per milliliter to at least about $6 \times 10^{10}$ colony-forming units per milliliter. In certain embodiments, fermentation products and compositions provided herein can comprise *Methylobacterium* that inhibit plant pathogenic fungi at a titer of at least about $1 \times 10^9$ colony-forming units per milliliter to at least about $3 \times 10^{10}$ colony-forming units per milliliter, at least about $1 \times 10^9$ colony-forming units per milliliter to at least about $4 \times 10^{10}$ colony-forming units per milliliter, or at least about $1 \times 10^9$ colony-forming units per milliliter to at least about $6 \times 10^{10}$ colony-forming units per milliliter. In certain embodiments, fermentation products and compositions provided herein will comprise *Methylobacterium* that inhibit plant pathogenic fungi at a titer of at least about $1 \times 10^{10}$ colony-forming units per milliliter to at least about $3 \times 10^{10}$ colony-forming units per milliliter, at least about $1 \times 10^{10}$ colony-forming units per milliliter to at least about $4 \times 10^{10}$ colony-forming units per milliliter, or at least about $1 \times 10^{10}$ colony-forming units per milliliter to at least about $6 \times 10^{10}$ colony-forming units per milliliter. In certain embodiments, fermentation products and compositions provided herein will comprise *Methylobacterium* that inhibit plant pathogenic fungi at a titer of, at least about $3 \times 10^{10}$ colony-forming units per milliliter to at least about $4 \times 10^{10}$ colony-forming units per milliliter, or at least about $3 \times 10^{10}$ colony-forming units per milliliter to at least about $6 \times 10^{10}$ colony-forming units per milliliter. In any of the aforementioned fermentation products or compositions, the indicated concentrations can be fungal inhibitory concentrations. In any of the aforementioned fermentation products or compositions, the fermentation products or compositions can be essentially free of contaminating microorganisms, can comprise *Methylobacterium* that are adhered to and/or associated with materials that the *Methylobacterium* are not are adhered to and/or associated with in nature, or any combination thereof.

Fermentation products and compositions with *Methylobacterium* that inhibit plant pathogenic fungi at a titer of greater than about $5 \times 10^7$, $1 \times 10^8$, or $5 \times 10^8$ colony-forming units per gram, at a titer of greater than about $1 \times 10^9$ colony-forming units per gram, at a titer of greater than about $1 \times 10^{10}$ colony-forming units per gram, at a titer of at least about $3 \times 10^{10}$ colony-forming units per gram are provided herein. In certain embodiments, fermentation products and compositions provided herein can comprise *Methylobacterium* that inhibit plant pathogenic fungi at a titer of at least about $5 \times 10^7$, $1 \times 10^8$, or $5 \times 10^8$ colony-forming units per gram to at least about $3 \times 10^{10}$ colony-forming units per gram, at least about $5 \times 10^7$, $1 \times 10^8$, or $5 \times 10^8$ colony-forming units per gram to at least about $4 \times 10^{10}$ colony-forming units per gram, or at least about $5 \times 10^7$, $1 \times 10^8$, or $5 \times 10^8$ colony-forming units per gram to at least about $6 \times 10^{10}$ colony-forming units per gram. In certain embodiments, fermentation products and compositions provided herein can comprise *Methylobacterium* that inhibit plant pathogenic fungi at a titer of at least about $1 \times 10^9$ colony-forming units per gram to at least about $3 \times 10^{10}$ colony-forming units per gram, at least about $1 \times 10^9$ colony-forming units per gram to at least about $4 \times 10^{10}$ colony-forming units per gram, or at least about $1 \times 10^9$ colony-forming units per gram to at least about $6 \times 10^{10}$ colony-forming units per gram. In certain embodiments, fermentation products and compositions provided herein will comprise *Methylobacterium* that inhibit plant pathogenic fungi at a titer of at least about $1 \times 10^{10}$ colony-forming units per gram to at least about $3 \times 10^{10}$ colony-forming units per gram, at least about $1 \times 10^{10}$ colony-forming units per gram to at least about $4 \times 10^{10}$ colony-forming units per gram, or at least about $1 \times 10^{10}$ colony-forming units per gram to at least about $6 \times 10^{10}$ colony-forming units per gram. In certain embodiments, fermentation products and compositions provided herein will comprise *Methylobacterium* that inhibit plant pathogenic fungi at a titer of, at least about $3 \times 10^{10}$ colony-forming units per gram to at least about $4 \times 10^{10}$ colony-forming units per gram, or at least about $3 \times 10^{10}$ colony-forming units per gram to at least about $6 \times 10^{10}$, $1 \times 10^{13}$, or $5 \times 10^{13}$ colony-forming units per gram. In any of the aforementioned fermentation products or compositions, the fermentation or composition can comprise a mono- or co-culture of *Methylobacterium* that is adhered to a solid substance. In any of the aforementioned fermentation products or compositions, the indicated concentrations can be fungal inhibitory concentrations. In any of the aforementioned fermentation products or compositions, the indicated concentrations can be fungal inhibitory concentrations. In any of the aforementioned fermentation products or compositions, the fermentation products or compositions can be essentially free of contaminating microorganisms, can comprise *Methylobacterium* that are adhered to and/or associated with materials that the *Methylobacterium* are not are adhered to and/or associated with in nature, or any combination thereof.

Solid substances with adherent *Methylobacterium* that inhibit plant pathogenic fungi can be obtained as fermentation products can be used to make various compositions useful for treating plants or plant parts to inhibit infection by plant pathogenic fungi. Alternatively, compositions provided herein comprising solid substances with *Methylobacterium* that inhibit plant pathogenic fungi or adherent *Methylobacterium* that inhibit plant pathogenic fungi can be used to treat plants or plant parts. Plants, plant parts, and, in particular, plant seeds that have been at least partially coated with the fermentation broth products or compositions comprising *Methylobacterium* that inhibit plant pathogenic fungi are thus provided. Also provided are processed plant products that contain the fermentation broth products or compositions with *Methylobacterium* that inhibit plant pathogenic fungi or adherent *Methylobacterium* that inhibit plant pathogenic fungi. Solid substances with adherent *Methylobacterium* that inhibit plant pathogenic fungi can be used to make various compositions that are particularly useful for treating plant seeds. Seeds that have been at least partially coated with the fermentation broth products or compositions are thus provided. Also provided are processed seed products, including, but not limited to, meal, flour, feed, and flakes that contain the fermentation broth products or compositions provided herein. In certain embodiments, the processed plant product will be non-regenerable (i.e. will be incapable of developing into a plant). In certain embodiments, the solid substance used in the fermentation product or composition that at least partially coats the plant, plant part, or plant seed or that is contained in the processed plant, plant part, or seed product comprises a solid substance and associated or adherent *Methylobacterium* that inhibit plant pathogenic fungi that can be readily identified by comparing a treated and an untreated plant, plant part, plant seed, or processed product thereof.

Compositions useful for treating plants or plant parts that comprise *Methylobacterium* that inhibit plant pathogenic fungi or a solid substance with adherent *Methylobacterium* that inhibit plant pathogenic fungi, emulsions containing the *Methylobacterium* that inhibit plant pathogenic fungi or combinations thereof can also comprise an agriculturally acceptable adjuvant or an agriculturally acceptable excipient. An agriculturally acceptable adjuvant or an agriculturally acceptable excipient is typically an ingredient that does not cause undue phytotoxicity or other adverse effects when exposed to a plant or plant part. In certain embodiments, the solid substance can itself be an agriculturally acceptable adjuvant or an agriculturally acceptable excipient so long as it is not bacteriocidal or bacteriostatic to the *Methylobacterium*. In other embodiments, the composition further comprises at least one of an agriculturally acceptable adjuvant or an agriculturally acceptable excipient. Any of the aforementioned compositions can also further comprise a pesticide. Pesticides used in the composition include, but are not limited to, an insecticide, a fungicide, a nematocide, and a bacteriocide. In certain embodiments, the pesticide used in the composition is a pesticide that does not substantially inhibit growth of the *Methylobacterium*. As *Methylobacterium* are gram negative bacteria, suitable bacteriocides used in the compositions can include, but are not limited to, bacteriocides that exhibit activity against gram positive bacteria but not gram negative bacteria. Compositions provided herein can also comprise a bacteriostatic agent that does not substantially inhibit growth of the *Methylobacterium*. Bacteriostatic agents suitable for use in compositions provided herein include, but are not limited to, those that exhibit activity against gram positive bacteria but not gram negative bacteria. Any of the aforementioned compositions can also be an essentially dry product (i.e. having about 5% or less water content), a mixture of the composition with an emulsion, or a suspension.

Agriculturally acceptable adjuvants used in the compositions that comprise *Methylobacterium* that inhibit plant pathogenic fungi, emulsions containing the *Methylobacterium* that inhibit plant pathogenic fungi, or combinations thereof include, but are not limited to, components that enhance product efficacy and/or products that enhance ease of product application. Adjuvants that enhance product efficacy can include various wetters/spreaders that promote adhesion to and spreading of the composition on plant parts, stickers that promote adhesion to the plant part, penetrants, extenders, and humectants that increase the density or drying time of sprayed compositions. Wetters/spreaders used in the compositions can include, but are not limited to, non-ionic surfactants, anionic surfactants, cationic surfactants, amphoteric surfactants, organo-silicate surfactants, and/or acidified surfactants. Stickers used in the compositions can include, but are not limited to, latex-based substances, terpene/pinolene, and pyrrolidone-based substances. Penetrants can include mineral oil, vegetable oil, esterified vegetable oil, organo-silicate surfactants, and acidified surfactants. Extenders used in the compositions can include, but are not limited to, ammonium sulphate, or menthene-based substances. Humectants used in the compositions can include, but are not limited to, glycerol, propylene glycol, and diethyl glycol. Adjuvants that improve ease of product application include, but are not limited to, acidifying/buffering agents, anti-foaming/de-foaming agents, compatibility agents, drift-reducing agents, dyes, and water conditioners. Anti-foaming/de-foaming agents used in the compositions can include, but are not limited to, dimethopolysiloxane. Compatibility agents used in the compositions can include, but are not limited to, ammonium sulphate. Drift-reducing agents used in the compositions can include, but are not limited to, polyacrylamides, and polysaccharides. Water conditioners used in the compositions can include, but are not limited to, ammonium sulphate.

Methods of treating plants and/or plant parts with the fermentation broths, fermentation broth products, and compositions comprising *Methylobacterium* that inhibit plant pathogenic fungi, or combinations thereof are also provided herein. Treated plants, and treated plant parts obtained therefrom, include, but are not limited to, corn, *Brassica* sp. (e.g., *B. napus, B. rapa, B. juncea*), alfalfa, rice, rye, sorghum, millet (e.g., pearl millet (*Pennisetum glaucum*)), proso millet (*Panicum miliaceum*), foxtail millet (*Setaria italica*), finger millet (*Eleusine coracana*), sunflower, safflower, soybean, tobacco, potato, peanuts, cotton, sweet potato (*Ipomoea batatus*), cassava, coffee, coconut, pineapple, citrus trees, cocoa, tea, banana, avocado, fig, guava, mango, olive, papaya, cashew, macadamia, almond, sugar beets, sugarcane, oats, barley, tomatoes, lettuce, green beans, lima beans, peas, cucurbits such as cucumber, cantaloupe, and musk melon, ornamentals, and conifers. Plant parts that are treated include, but are not limited to, leaves, stems, flowers, roots, seeds, fruit, tubers, coleoptiles, and the like. Ornamental plants and plant parts that can be treated include, but are not limited to azalea, hydrangea, hibiscus, roses, tulips, daffodils, petunias, carnation, poinsettia, and chrysanthemum. Conifer plants and plant parts that can be treated include, but are not limited to, pines such as loblolly pine, slash pine, ponderosa pine, lodge pole pine, and Monterey pine; Douglas-fir; Western hemlock; Sitka spruce; redwood; true firs such as silver fir and balsam fir; and cedars such as Western red cedar and Alaska yellow-cedar. Turfgrass plants and plant parts that can be treated include, but are not limited to, annual bluegrass, annual ryegrass, Canada bluegrass, fescue, bentgrass, wheatgrass, Kentucky bluegrass, orchard grass, ryegrass, redtop, Bermuda grass, St. Augustine grass, and zoysia grass. In certain embodiments, the treated plant or plant part is a cereal plant or plant part selected from the group consisting of a rice, wheat, corn, barley, millet, sorghum, oat, and rye plant or plant part. Seeds or other propagules of any of the aforementioned plants can be treated with the fermentation broths, fermentation broth products, fermentation products, and/or compositions provided herein.

In certain embodiments, plants and/or plant parts are treated by applying the fermentation broths, fermentation broth products, fermentation products, and compositions that comprise *Methylobacterium* that inhibit plant pathogenic fungi, or combinations thereof as a spray. Such spray applications include, but are not limited to, treatments of a single plant part or any combination of plant parts. Spraying can be achieved with any device that will distribute the fermentation broths, fermentation broth products, fermentation products, and compositions to the plant and/or plant part(s). Useful spray devices include a boom sprayer, a hand or backpack sprayer, crop dusters (i.e. aerial spraying), and the like. Spraying devices and or methods providing for application of the fermentation broths, fermentation broth products, fermentation products, and compositions to either one or both of the adaxial surface and/or abaxial surface can also be used. Plants and/or plant parts that are at least partially coated with any of a biphasic fermentation broth, a fermentation broth product, fermentation product, or compositions that comprise a solid substance with *Methylobacterium* that inhibit plant pathogenic fungi adhered thereto are also provided herein. Also provided herein are processed plant products that comprise a solid substance with *Methylobacterium* that inhibit plant pathogenic fungi adhered thereto.

In certain embodiments, seeds are treated by exposing the seeds to the fermentation broths, fermentation broth products, fermentation products, and compositions that comprise *Methylobacterium* that inhibit plant pathogenic fungi, or combinations thereof. Seeds can be treated with the fermentation broths, fermentation broth products, and compositions provided herein by methods including, but not limited to, imbibition, coating, spraying, and the like. Seed treatments can be effected with both continuous and/or a batch seed treaters. In certain embodiments, the coated seeds can be prepared by slurrying seeds with a coating composition containing a fermentation broth, fermentation broth product, or compositions that comprise the solid substance with *Methylobacterium* that inhibit plant pathogenic fungi and air drying the resulting product. Air drying can be accomplished at any temperature that is not deleterious to the seed or the *Methylobacterium*, but will typically not be greater than 30 degrees Centigrade. The proportion of coating that comprises a solid substance and *Methylobacterium* that inhibit plant pathogenic fungi includes, but is not limited to, a range of 0.1 to 25% by weight of the seed, 0.5 to 5% by weight of the seed, and 0.5 to 2.5% by weight of seed. In certain embodiments, a solid substance used in the seed coating or treatment will have *Methylobacterium* that inhibit plant pathogenic fungi adhered thereon. In certain embodiments, a solid substance used in the seed coating or treatment will be associated with *Methylobacterium* that inhibit plant pathogenic fungi and will be a fermentation broth, fermentation broth product, or composition obtained by the methods provided herein. Various seed treatment compositions and methods for seed treatment disclosed in U.S. Pat. Nos. 5,106,648; 5,512,069; and 8,181,388 are incorporated herein by reference in their entireties and can be adapted for use with fermentation products or compositions provided herein. In certain embodiments, the composition used to treat the seed can contain agriculturally acceptable excipients that include, but are not limited to, woodflours, clays, activated carbon, diatomaceous earth, fine-grain inorganic solids, calcium carbonate and the like. Clays and inorganic solids that can be used with the fermentation broths, fermentation broth products, or compositions provided herein include, but are not limited to, calcium bentonite, kaolin, china clay, talc, perlite, mica, vermiculite, silicas, quartz powder, montmorillonite and mixtures thereof. Agriculturally acceptable adjuvants that promote sticking to the seed that can be used include, but are not limited to, polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxy methylcelluloses, hydroxypropylcellulose, hydroxymethylpropylcelluloses, polyvinyl pyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethylcellulose, chitosan, polyethylene oxide, acrylamide polymers and copolymers, polyhydroxyethyl acrylate, methylacrylamide monomers, alginate, ethylcellulose, polychloroprene and syrups or mixtures thereof. Other useful agriculturally acceptable adjuvants that can promote coating include, but are not limited to, polymers and copolymers of vinyl acetate, polyvinylpyrrolidone-vinyl acetate copolymer and water-soluble waxes. Various surfactants, dispersants, anticaking-agents, foam-control agents, and dyes disclosed herein and in U.S. Pat. No. 8,181,388 can be adapted for use with a fermentation products or compositions provided herein.

Provided herein are compositions that comprise *Methylobacterium* that inhibit plant pathogenic fungi and that provide control of plant pathogenic fungal infections of plants, plant parts, and plants obtained therefrom relative to untreated plants, plant parts, and plants obtained therefrom that have not been exposed to the compositions. In certain embodiments, plant parts, including, but not limited to, a seed, a leaf, a fruit, a stem, a root, a tuber, or a coleoptile can be treated with the compositions provided herein to control fungal disease. Treatments or applications can include, but are not limited to, spraying, coating, partially coating, immersing, and/or imbibing the plant or plant parts with the compositions provided herein. In certain embodiments, a seed, a leaf, a fruit, a stem, a root, a tuber, or a coleoptile can be immersed and/or imbibed with a liquid, semi-liquid, emulsion, or slurry of a composition provided herein. Such seed immersion or imbibition can be sufficient to provide for fungal disease inhibition in a plant or plant part in comparison to an untreated plant or plant part. Such fungal disease inhibition includes, but is not limited to decreases in fungal growth and/or the adverse effects of fungal growth relative to untreated plants. In certain embodiments, plant seeds can be immersed and/or imbibed for at least 1, 2, 3, 4, 5, or 6 hours. Such immersion and/or imbibition can, in certain embodiments, be conducted at temperatures that are not deleterious to the plant seed or the *Methylobacterium*. In certain embodiments, the seeds can be treated at about 15 to about 30 degrees Centigrade or at about 20 to about 25 degrees Centigrade. In certain embodiments, seed imbibition and/or immersion can be performed with gentle agitation.

Amounts of the compositions that comprise *Methylobacterium* that inhibit plant pathogenic fungi that are sufficient to provide for an inhibition of fungal infection of a plant or plant part can thus be determined by measuring any or all of fungal growth and/or the adverse effects of fungal growth in treated plants or plant parts relative to untreated plants or plant parts. Adverse effects of fungal growth in a plant that can be measured include any type of plant tissue damage or necrosis, any type of plant yield reduction, any reduction in the value of the crop plant product, and/or production of undesirable fungal metabolites or fungal growth by-products including, but not limited to, mycotoxins. Mycotoxins comprise a number of toxic molecules produced by fungal species, including, but not limited to, polyketides (including aflatoxins, demethylsterigmatocystin, O-methylsterigmatocystin etc.), fumonisins, alperisins (e.g., $A_1$, $A_2$, $B_1$, $B_2$), sphingofungins (A, B, C and D), trichothecenes, fumifungins, and the like. Methods of quantitating mycotoxin levels are widely documented. Moreover, commercial kits for measurement of the mycotoxins such as aflatoxin, fumonisin, deoxynivalenol, and zearalenone are also available (VICAM, Watertown, Mass., USA).

Compositions provided herein comprising *Methylobacterium* that inhibit plant pathogenic fungi are therefore expected to be useful in inhibiting fungal growth and/or infection in a wide variety of plant pathogenic fungi, including, but not limited to the anamorphic and/or teleomorphic stages of those phytopathogenic fungi in the following genera and species: *Alternaria* (*Alternaria alternata; Alternaria brassicicola; Alternaria solani*); *Ascochyta* (*Ascochyta pisi*); *Bipolaris* (*Bipolaris maydis*); *Botrytis* (*Botrytis cinerea*); *Bremia* (*Bremia lactucae*); *Cercospora* (*Cercospora kikuchii; Cercospora zeae-maydis*); *Cochliobolus* (*Colchliobolus maydis; Cochliobolus heterostrophus; Cochliobolus carbonum*); *Colletotrichum* (*Colletotrichum lindemuthianum; Colletotrichum graminicola; Colletotrichum cereale*); *Diplodia* (*Diplodia maydis*); *Erysiphe* (*Erysiphe graminis* f. sp. *graminis; Erysiphe graminis* f. sp. *hordei*); *Exserohilum* (*Exserohilum turcicum*); *Fusarium* (*Fusarium nivale; Fusarium oxysporum; Fusarium graminearum; Fusarium culmorum; Fusarium solani; Fusarium moniliforme; Fusarium virguliforme*); *Gaeumanomyces* (*Gaeumanomyces graminis* f. sp. *tritici*); *Macrophomina* (*Macrophomina phaseolina*); *Magnaporthe* (*Magnaporthe oryzae; Magnaporthe grisea*); *Nectria* (*Nectria haematococca*); *Peronospora* (*Peronospora manshurica; Peronospora tabacina*); *Phakopsora* (*Phakopsora pachyrhizi*); *Phialopora* (*Phialophora gregata*); *Phoma* (*Phoma betae*); *Phymatotrichum* (*Phymatotrichum omnivorum*); *Phytophthora* (*Phytophthora cinnamomi; Phytophthora cactorum; Phytophthora phaseoli; Phytophthora parasitica; Phytophthora citrophthora; Phytophthora megasperma* f. sp. *sojae; Phytophthora infestans*); *Plasmopara* (*Plasmopara viticola*); *Podosphaera* (*Podosphaera leucotricha*); *Puccinia* (*Puccinia sorghi; Puccinia striiformis; Puccinia graminis* f sp. *tritici; Puccinia asparagi; Puccinia recondita; Puccinia arachidis; Puccinia coronata*); *Pythium* (*Pythium aphanidermatum; Pythium ultimum*); *Pyrenophora* (*Pyrenophora tritici-repentis*); *Rhizoctonia* (*Rhizoctonia solani; Rhizoctonia cerealis*); *Sclerotium* (*Sclerotium rolfsii*); *Sclerotinia* (*Sclerotinia sclerotiorum; Sclerotinia homoeocarpa*); *Septoria* (*Septoria lycopersici; Septoria glycines; Septoria nodorum; Septoria tritici*); *Setosphaeria* (*Setosphaeria turcica*); *Stagonospora* (*Stagonospora nodorum*); *Thielaviopsis* (*Thielaviopsis basicola*); *Uncinula* (*Uncinula necator*); *Ustilago* (*Ustilago maydis*); *Venturia* (*Venturia inaequalis*); *Verticillium* (*Verticillium dahliae; Verticillium albo-atrum*). Compositions provided herein comprising *Methylobacterium* that inhibit plant pathogenic fungi are also expected to be useful in inhibiting fungal growth and/or infection by *Fusarium graminearum, Fusarium verticillioides* and/or *Fusarium proliferatum*. Compositions provided herein comprising *Methylobacterium* that inhibit fungal growth and/or infection by *Fusarium graminearum, Fusarium verticillioides* and/or *Fusarium proliferatum* can be used to control infections of cereal plants infected by these fungi. Infections of cereal plants selected from the group consisting of a rice, wheat, corn, barley, millet, sorghum, oat, and rye plants by *Fusarium* sp can be controlled by the compositions provided herein. In any of the aforementioned embodiments, the plant pathogenic fungus that is inhibited can be in its anamorphic form, its teleomorphic form, or in both its anamorphic and teleomorphic forms. Certain *Methylobacterium* isolates or combinations of isolates can also be used to inhibit certain plant pathogenic fungi in certain crops as disclosed in Table 2. In certain embodiments where a combination of isolates are used (e.g., NLS0066 and NLS0017 or NLS0089 and NLS0020), the isolates can be applied either simultaneously or sequentially. In certain embodiments where a combination of isolates are used (e.g., NLS0066 and NLS0017 or NLS0089 and NLS0020), the isolates can be applied in either the same mode(s) (e.g., via a seed treatment, a foliar application, or in furrow) or by distinct modes.

TABLE 2

*Methylobacterium* isolates and combinations of isolates for use in controlling certain plant pathogenic fungi in certain crops

| NLS Isolate(s) | Crop | Pathogen | Disease Common Name(s) | Mode(s) of Application |
|---|---|---|---|---|
| NLS066 | Wheat | *Fusarium graminearum* | *Fusarium* head blight | Seed treatment; foliar |
| | Corn | *Cercospora zeae-maydis* | Gray leaf spot | In-furrow; foliar |
| | | *Colletotrichum graminicola* | Anthracnose leaf blight and stalk rot | |
| NLS0066 + NLS0017 | Wheat | *Fusarium graminearum* | *Fusarium* head blight | Seed treatment; foliar |
| | Corn | *Cercospora zeae-maydis* | Gray leaf spot | In-furrow; foliar |
| | | *Colletotrichum graminicola* | Anthracnose leaf blight and stalk rot | |

TABLE 2-continued

*Methylobacterium* isolates and combinations of isolates for use in controlling certain plant pathogenic fungi in certain crops

| NLS Isolate(s) | Crop | Pathogen | Disease Common Name(s) | Mode(s) of Application |
|---|---|---|---|---|
| NLS0089 | Wheat | *Fusarium graminearum* | *Fusarium* head blight | Seed treatment; foliar |
| | | *Septoria tritici* *Stagonospora nodorum* | *Septoria*/*Stagonospora* blotch | |
| | | *Pythium* spp. | *Pythium* root rot | |
| | | *Rhizoctonia solani* | *Rhizoctonia* root rot | |
| | | *Fusarium* spp. | *Fusarium* root, crown, and foot rot | |
| | | *Magnaportha grisea* | Head blast | |
| | | *Pyrenophora tritici-repentis* | Tan spot | |
| | | *Microdochium nivale* | Snow mold | |
| | Soybean | *Sclerotinia sclerotiorum* | *Sclerotinia* white mold/stem rot; | Seed treatment; foliar |
| | | *Cercospora sojina* | Frogeye leaf spot; | |
| | | *Cercospora kikuchii* | *Cercospora* leaf blight and purple seed stain | |
| | | *Fusarium* spp. | *Fusarium* seed rot, blight/wilt, root rot and pod and collar rot | |
| | | *Rhizoctonia solani* | *Rhizoctonia* damping off and root rot | |
| | | *Fusarium virguliforme* | Sudden death syndrome | |
| | | *Pythium* spp. | *Pythium* root rot | |
| | | *Rhizoctonia solani* | *Rhizoctonia* crown and root rot | |
| | | *Fusarium* spp. | *Fusarium* root rot; | |
| | | *Colletotrichum graminicola* | Anthracnose leaf blight and stalk rot | |
| | Corn | *Cercospora zeae-maydis* | Gray leaf spot | In-furrow; foliar |
| | | *Gibberella zeae* | *Gibberella* stalk rot; | |
| | | *Fusarium* spp. | *Fusarium* stalk rot; | |
| | | *Pythium* spp. | *Pythium* stalk rot | |
| NLS0089 + NLS0020 | Wheat | *Fusarium graminearum* | *Fusarium* head blight | |
| | | *Septoria tritici* *Stagonospora nodorum* | *Septoria*/*Stagonospora* blotch | |
| | | *Pythium* spp. | *Pythium* root rot | |
| | | *Rhizoctonia solani* | *Rhizoctonia* root rot | |
| | | *Fusarium* spp. | *Fusarium* root, crown, and foot rot | |
| | | *Magnaportha grisea* | Head blast | |
| | | *Pyrenophora tritici-repentis* | Tan spot | |
| | | *Microdochium nivale* | Snow mold | |
| | Soybean | *Sclerotinia sclerotiorum* | *Sclerotinia* white mold/stem rot; | |
| | | *Cercospora sojina* | Frogeye leaf spot; | |
| | | *Cercospora kikuchii* | *Cercospora* leaf blight and purple seed stain | |
| | | *Fusarium* spp. | *Fusarium* seed rot, blight/wilt, root rot and pod and collar rot | |
| | | *Rhizoctonia solani* | *Rhizoctonia* damping off and root rot | |
| | | *Fusarium virguliforme* | Sudden death syndrome | |
| | | *Pythium* spp. | *Pythium* root rot | |
| | | *Rhizoctonia solani* | *Rhizoctonia* crown and root rot | |
| | | *Fusarium* spp. | *Fusarium* root rot; | |
| | | *Colletotrichum graminicola* | Anthracnose leaf blight and stalk rot | |
| | Corn | *Cercospora zeae-maydis* | Gray leaf spot | |
| | | *Gibberella zeae* | *Gibberella* stalk rot; | |
| | | *Fusarium* spp. | *Fusarium* stalk rot; | |
| | | *Pythium* spp. | *Pythium* stalk rot | |

In certain embodiments, an amount of a composition provided herein that is sufficient to provide for inhibition of fungal infection in a plant or plant part can be a composition with *Methylobacterium* that inhibit plant pathogenic fungi at a titer of at least about $5 \times 10^8$ colony-forming units per milliliter, at least about $1 \times 10^9$ colony-forming units per milliliter, at least about $1 \times 10^{10}$ colony-forming units per milliliter, or at least about $3 \times 10^{10}$ colony-forming units per milliliter. In certain embodiments, an amount of a composition provided herein that is sufficient to provide for inhibition of fungal disease in a plant or plant part can be a composition with *Methylobacterium* that inhibit plant pathogenic fungi at a titer of about $5 \times 10^8$ colony-forming units per milliliter to at least about $6 \times 10^{10}$ colony-forming units per milliliter. In certain embodiments, an amount of a composition provided herein that is sufficient to provide for inhibition of fungal disease in a plant or plant part can be a fermentation broth product with a *Methylobacterium* that inhibit plant pathogenic fungi titer of a solid phase of that product is at least about $1 \times 10^7$, $5 \times 10^7$, $1 \times 10^8$, or $5 \times 10^8$ colony-forming units per gram to at least about $6 \times 10^{10}$ $1 \times 10^{13}$, or $5 \times 10^{13}$ colony-forming units of *Methylobacterium* per gram of the solid phase wherein a mono-culture or co-culture of *Methylobacterium* that inhibit plant pathogenic fungi is adhered thereto. In certain embodiments, an amount of a composition provided herein that is sufficient to provide for inhibition of fungal disease in a plant or plant part can be a composition with a *Methylobacterium* titer of at least about $1 \times 10^7$, $5 \times 10^7$, $1 \times 10^8$, or $5 \times 10^8$ colony-forming units per gram to at least about $6 \times 10^{10}$, $1 \times 10^{13}$, or $5 \times 10^{13}$ colony-forming units of *Methylobacterium* per gram of particles in the composition containing the particles that comprise a solid substance wherein a mono-culture or co-culture of *Methylobacterium* that inhibit plant pathogenic fungi is adhered thereto. In any of the aforementioned compositions, the indicated concentrations can be fungal inhibitory concentrations.

EXAMPLES

The following examples are included to demonstrate various embodiments. It will be appreciated by those of skill in the art that the techniques disclosed in the following examples represent techniques discovered by the Applicants to function well. However, those of skill in the art should, in light of the instant disclosure, appreciate that many changes can be made in the specific embodiments that are disclosed, while still obtaining like or similar results, without departing from the scope of the disclosure.

Example 1. Suppression of *Fusarium graminearum* by PPFMs

PPFM cultures for seed treatment were grown in AMS-GP medium amended with 0.2% w/v diatomaceous earth (International Patent Application PCT/US13/43722, filed May 31, 2013). Cells were harvested by centrifugation and resuspended in water to a final concentration of approximately $1.3 \times 10^8$ CFU/ml. *Brachypodium distachyon* seeds of inbred line Bd21-3 were treated by incubating overnight in plastic germination boxes between two sheets of germination paper saturated with 30 ml of the PPFM suspension. The germination boxes were placed in the dark at 4° C. for the duration of the seed treatment period. Seeds for the control group were treated similarly, except that water was applied to germination paper.

Treated seeds were planted into soilless potting media and grown in a controlled environment growth chamber (24° C., 50% relative humidity, and light intensity of 200 µmol/m²/s) with a 20 h day-length to promote flowering. Forty-two±two days after planting, reproductively mature *B. distachyon* plants were moved to the greenhouse (21-24° C., 40% relative humidity). In order to allow plants time to acclimate to greenhouse conditions, inoculations were performed two days after transfer to the greenhouse.

*Fusarium graminearum* was maintained on potato dextrose agar (PDA). One week prior to the intended inoculation date, three 8×8 mm agar plugs from the advancing edge of an approximately one-week old *F. graminearum* colony were transferred to 75 ml CMC medium (Cappellini and Peterson, Mycologia 57: 962-966, 1965) in a 250 ml flask. Flasks were wrapped in tin foil and incubated at ambient temperature for six days with shaking (175 rpm). After the sixth day, conidia were harvested by filtering through a double-layer of sterile cheesecloth, followed by centrifugation. The pelleted conidia were then resuspended in sterile deionized (DI) water and the conidial concentration was determined using a hemacytometer. For inoculation, a final concentration of $1 \times 10^5$ conidia/ml was prepared in sterile DI water amended with 0.01% Tween (v/v).

Plants were inoculated by spraying the conidial suspension directly onto spikelets until droplet run-off. Control plants received a mock-inoculation treatment of sterile DI water amended with 0.01% Tween 20. Immediately following inoculation, individual plants were bagged to maintain high humidity and prevent cross-contamination. All plants were then arranged in a randomized complete block design with six replications. Humidity domes were placed over each flat for the first five days to maintain relative humidity near 100%. At 7 days post inoculation, disease incidence and severity were rated for each plant. Incidence was rated as the number of symptomatic spikelets affected divided by the total number of spikelets per plant. The total area of the spikelets per plant showing disease symptoms was used to rate severity and was scored on a 0-5 scale with 0 indicating absence of spikelet symptoms, 1=1-20%, 2=21-40, 3=41-60%, 4=61-80%, and 5=81-100% symptomatic spikelet area per plant.

Of the four NLS strain seed treatments tested (PPFM strains NLS0017, NLS0020, NLS0037, and NLS0066) only the plants from seeds treated with PPFM strain NLS0066 exhibited significantly reduced (95-99% confidence interval) FHB symptom incidence (Table 3) and severity (Table 4) relative to the DI water-treated control. The reduction was at or near 50% for both disease metrics. Seed treatment with PPFM strain NLS0017 decreased both symptom severity and incidence relative to control plants approximately 27%; however, this difference was not significant at the 95% confidence limit. PPFM strains NLS0020 and NLS0037 did not affect either spikelet incidence or symptom severity.

TABLE 3

Spikelet Incidence

| Treatment | Inoculation | Mean | SE | % Difference from Control | Significance |
|---|---|---|---|---|---|
| Water | *F. graminearum* | 27.78 | 3.68 | 0.00 | NS |
| NLS0017 | *F. graminearum* | 20.27 | 7.15 | −27.03 | NS |
| NLS0020 | *F. graminearum* | 30.27 | 5.25 | +8.96 | NS |

TABLE 3-continued

Spikelet Incidence

| Treatment | Inoculation | Mean | SE | % Difference from Control | Significance |
|---|---|---|---|---|---|
| NLS0037 | F. graminearum | 33.44 | 3.34 | +20.27 | NS |
| NLS0066 | F. graminearum | 14.67 | 6.21 | −47.20 | >95% |

TABLE 4

Symptom Severity

| Treatment | Inoculation | Mean | SE | % Difference from Control | Significance |
|---|---|---|---|---|---|
| Water | F. graminearum | 2.12 | 0.33 | 0.00 | NS |
| NLS0017 | F. graminearum | 1.56 | 0.26 | −26.50 | NS |
| NLS0020 | F. graminearum | 1.78 | 0.31 | −16.04 | NS |
| NLS0037 | F. graminearum | 2.17 | 0.26 | +2.36 | NS |
| NLS0066 | F. graminearum | 1.06 | 0.21 | −50.00 | >99% |

Example 2. Identification of PPFM Strains that Confer Resistance to FHB of Wheat in Growth Chamber and Field Tests

*Fusarium* Head Blight (FHB) susceptible wheat cultivar Bobwhite or another FHB-susceptible cultivar will be used for growth chamber studies. For each PPFM isolate to be tested, the seeds will be planted without any PPFM treatment and grown in the growth chamber. The spikes of fifteen plants will be sprayed with a suspension of each PPFM strain at $10^6$ or $10^8$ cfu/ml. Two spikes from each plant will be point-inoculated by injecting the individual florets in the middle of the spike at anthesis with a 10 μl of conidial suspension of *F. graminearum* PH-1 or another virulent *F. graminearum* isolate(s) ($10^5$ spores/ml) or water control (mock) in 0.01% Triton 60 or Tween 20 solution (Goswami and Kistler, 2005). After inoculation, the plants will be placed in a growth chamber at 16° C. for 8 h (night) and 18° C. for 16 h (day). To ensure proper disease severity, the spikes will be covered with plastic bags for 48 h to increase the humidity. The first disease evaluation will be performed 7 days after inoculation. The number of spikelets that exhibit symptoms will be counted for each inoculated spike and recorded. Evaluation will be repeated at 14 days after inoculation. Disease severity will be calculated as percentage of diseased spikelets per spike (disease severity rating) for each date of evaluation. To test the overall treatment effect, area under the disease progress curve (AUDPC) will be calculated for each plant. We anticipate that plants treated with a few PPFM strains will have much lower disease scores (AUDPC) than the control plants. We anticipate that some PPFM strains applied as floral spray will provide resistance to FHB in these growth chamber tests.

PPFM isolates that have been determined to provide FHB resistance in the growth chamber tests will be advanced for testing in the field for their ability to provide FHB resistance. Field tests will be conducted in two or more locations. Field experiments will be conducted using a randomized complete block design with four rows and six replications per treatment. Fifty PPFM-treated seeds per replication will be sown at each location. Four border rows will surround the experiment site and will not be treated with PPFMs. About 2 weeks before anticipated anthesis, yellow dent air-dried corn kernels colonized by a single, aggressive isolate of *F. graminearum* will be spread uniformly at ~25 kernels per m$^2$ throughout the test area. Perithecia will appear on the kernels within a few days and start releasing ascospores at the time of anthesis when wheat is most susceptible to infection by this pathogen. At the time of flowering spikes, PPFM suspension of each strain at $1\times10^8$ cfu/ml in water containing 0.04% Tween 80 or similar surfactant will be applied using a $CO_2$ backpack sprayer as described (Schisler et al., 2002). The control treatments will be sprayed with water containing 0.04% Tween 80 or similar surfactant but no PPFM. During anthesis, spikes will be kept moist by using small, overhead sprinklers for 3 min every hour from morning to dusk.

When plants reach the late milk development stage in the field, assessments of FHB incidence and severity will be made by evaluating 60 heads per replicate as described (Stack and McMullen, 1995). Wheat spikes will be harvested by hand, threshed and evaluated for 100-kernel weight. Ten to 20 g samples of each replicate will be analyzed for its deoxynivalenol (DON) content using the Veratox™ 5/5 quantitative DON test kit (Neogen Corp., Lansing, Mich., USA).

The statistical analysis of the disease incidence and severity and of the DON data will be performed with PROC GLIMMIX of SAS (SAS Institute, Research Triangle Park, N.C.) or the 'lme' and related packages in R (http://www.R-project.org). Data will be considered significantly different at a P value of <0.05. Correlation analysis will be conducted on means for FHB severity and DON content using PROC REG of SAS (SAS Institute, Research Triangle Park, N.C.), which calculates Pearson's correlation coefficient.

(1) Cappellini R A, Peterson J L (1965) Macroconidium formation in submerged cultures by a non-sporulating strain of *Gibberella zeae*. Mycologia 57: 962-966.

(2) Spelbrink R G, Dilmac N, Allen A, Smith T J, Shah D M, et al. (2004) Differential antifungal and calcium channel-blocking activity among structurally related plant defensins. Plant Physiol 135: 2055-2067.

(3) Broekaert W F, Terras F R, Cammue B P, Vanderleyden J (1990) An automated quantitative assay for fungal growth inhibition. FEMS Microbiology Letters 69: 55-60.

(4) Holland, M. A, Polacco, J. C. (1994) PPFMs and other covent contaminants: Is there more to plant physiology than just plant. Annu. Rev. Plant Physiol. Plant Mol Biol 45: 197-208.

(5) Jacobson, B. J. (2006) Biological control of plant diseases by phyllosphere applied biological control agents. In M J Bailey, A K Lilley, T M Timms-Wison, P T N Spencer-Phillips, eds, Microbial ecology of aerial strains in a controlled model system. CAB International, United Kingdom, Wallingford, pp 133-147.

Example 3. Suppression of *Fusarium* Headblight on Greenhouse Grown Wheat

Frozen PPFM concentrates ($1\times10^8$ CFU/mL) were thawed to room temperature immediately prior to use in seed treatment. PPFM concentrates were then vortexed for 10 seconds and 75 μL of each treatment was pipetted into a 15 mL conical tube containing 100 seeds of spring wheat (*Triticum aestivum* L., cv. 'Bobwhite'). To simulate standard industry seed treatments, 66.8 uL of an agricultural polymer solution (Flo Rite 1706 Plantability Polymer, BASF, North Carolina, USA), prepared by combining 6.1 mL polymer with 40 mL deionized water, was added to each treatment tube. Tubes were capped and vortexed for approximately 90 seconds to thoroughly coat seeds. Treated seeds were allowed to air dry under a Kimwipe™ on a lab benchtop prior and a maintained at room temperature prior to use. All seeds were used within one week of treatment. Excess seed were checked for PPFM concentration and viability by placing ten seeds into sterile distilled water, vortexing for ten second, and plating 100 uL of the resulting seed wash onto PPFM-selective medium. Control seeds were treated with a solution of PPFM growth medium and polymer solution.

Treated seeds were planted into a 50/50 mix of soilless potting media/field soil and grown in an air-conditioned greenhouse (70° F. night/68° F. day, 40-90% RH, 16 h day-length) until anthesis. Plants received water daily and fertilizer solution two times per week.

*Fusarium graminearum* was maintained on potato dextrose agar (PDA). One week prior to the intended inoculation date, three 8×8 mm agar plugs from the advancing edge of an approximately one-week old *F. graminearum* colony were transferred to 75 mL CMC medium (Cappellini and Peterson, 1965) in a 250 mL flask. Flasks were incubated at ambient temperature for six days with shaking (175 rpm). After the sixth day, conidia were harvested by filtering through a double-layer of sterile cheesecloth, followed by centrifugation. The pelleted conidia were then resuspended in sterile deionized (DI) water and the conidial concentration was determined using a hemacytometer. For inoculation, a final concentration of $1.0\text{-}2.0 \times 10^5$ conidia/ml was prepared in sterile DI water amended with 0.01% Tween (v/v).

Plants were inoculated by spraying the conidial suspension directly onto spikelets with an airbrush calibrated to 20 psi. Ten mL of conidial suspension were applied evenly across each flat of 18 pots. Control plants received a mock-inoculation treatment of sterile DI water amended with 0.01% Tween. Just prior to inoculation, pots of each treatment were arranged in a randomized complete block design with eighteen replications per treatment. Plants were placed in a mist chamber at 90% relative humidity for 72 h following inoculation then moved to a greenhouse benchtop. At ten days post inoculation, disease severity was rated for each plant. The total area of each head with visible disease symptoms was rated on a 0-100% scale and the individual severity values for heads within a pot was averaged in final analysis.

NLS0089 demonstrated consistent disease suppression relative to control (GlyC) plants, by suppressing disease in four of six trials (Table 5).

TABLE 5

Greenhouse Testing for *Fusarium* Head Blight control

| Treatment | Rep 1 | Rep 2 | Rep 3 | Rep 4 | Rep 5 |
|---|---|---|---|---|---|
| GlyC | 79.5 | 41.9 | 86.7 | NA | NA |
| NLS0089 | 76.8 | 40.0 | 90.1 | NA | NA |
| GlyC | 19.7 | 46.6 | 43.4 | 13.3 | NA |
| NLS0020 | 20.8 | 54.2 | 49.6 | 10.8 | NA |
| NLS0037 | 11.4 | 52.9 | 57.8 | 12.2 | NA |
| NLS0066 | 24.4 | 52.1 | 50 | 10.3 | NA |
| NLS0089 | 19.1 | 56.5 | 47.9 | 6.8 | NA |
| GlyC | 20.4 | 5.2 | 10.7 | NA | NA |
| NLS0017 | 26.3 | 3.6 | 16.2 | NA | NA |
| NLS0017 + 21 | 38.6 | 11.6 | 15.3 | NA | NA |
| NLS0021 | 30.5 | 12.7 | 12.6 | NA | NA |

Example 4. Suppression of FHB in the Field by PPFM Seed Treatment

A field trial to assess *Fusarium* Head Blight (FHB) suppression by PPFM seed treatment was conducted in Brookings, S. Dak. in the spring of 2015. Spring wheat cultivar 'Select' was used for the trial and seeds were sown in the first week of July, with harvest in late September. Due to the late planting date of this trial, yield data were not usable.

The trial was arranged as a randomized complete block design (RBCD) with ten replications. Each block consisted of four 10 foot rows with 254 seeds per plot. In-row seed spacing was ~8.5" apart with 2.11 seeds per linear inch. Two blanks row spaces were left between plots within a replication and a blank plot space was left between replications to provide separation between treatments. Disease rating data were collected only from the two center rows within plots. Throughout the trial, plots were maintained using standard agronomic practices with the exception that no foliar fungicide applications were made for disease control.

PPFM were applied to wheat seed using standard industry treatment practices and were planted within 24 h of seed treatment. The base treatment consisted of Rancona® Summit fungicide for control of seedling disease (8.33 fl oz/cwt), Gaucho® 480 insecticide (3.0 fl oz/cwt), and industry standard seed treatment polymer (1.0 fl oz/cwt; Flo Rite 1706 Plantability Polymer, BASF Corporation, North Carolina, USA). Concentrated PPFM treatments were supplied frozen on dry ice and thawed immediately prior to use in seed treatment. PPFM solutions were applied to achieve a target of $1.0 \times 10^6$ CFUs of PPFM bacteria/seed. Treatments are listed in Table 6.

TABLE 6

| Treatment No | Treatment | Product |
|---|---|---|
| 1 | Base | Rancona ® Summit Gaucho ® 480 Polymer (FR 1706) |
| 2 | Base + NLS0017 | Rancona ® Summit Gaucho ® 480 Polymer (FR 1706) NLS0017 |
| 3 | Base + NLS0020 | Rancona ® Summit Gaucho 480 Polymer (FR 1706) NLS0020 |
| 4 | Base + NLS0066 | Rancona Summit Gaucho ® 480 Polymer (FR 1706) NLS0066 |
| 5 | Base + NLS0089 | Rancona Summit Gaucho ® 480 Polymer (FR 1706) NLS0089 |
| 6 | Base + NLS0017 NLS0066 | Rancona Summit Gaucho ® 480 Polymer (FR 1706) NLS0017 NLS0066 |

Prevailing environmental conditions were highly favorable to disease, resulting in strong natural FHB pressure. Artificial inoculation in the form of locally sourced *Fusarium graminearum* conidia was applied to half of the replications in the trial. Inoculum was applied at a concentration of $1 \times 10^4$ conidia/mL and 25 mL were applied per plot. Disease data for inoculated and naturally infected plots were not significantly different; thus, data points were pooled for final analysis. Disease ratings were taken approximately one month following inoculation. Metrics collected were percent FHB incidence, determined on a plot level by visual inspection, and disease severity, determined by rating a sample of 20 individual detached heads collected from the field. A disease index was also calculated for each plot using the formula: [(Incidence×Severity)/100].

Disease data were analyzed using the JMP (version. 11) statistical discovery software package from SAS (SAS Institute, Research Triangle Park, N.C.). Data were analyzed using a mixed model with 'treatment' and 'inoculation' specified as fixed effects and 'block' as a random effect. After the determination that 'inoculation' had no significant effect on disease outcomes, this factor was dropped from the model. A summary of results is provided in Table 7.

TABLE 7

| Treatment | FHB Incidence (%) | FHB Severity (%) | Disease Index |
|---|---|---|---|
| Control (Base) | 94.2 | 55.42 | 52.15 |
| NLS0017 | 84.3***$^a$ | 52.97 | 44.54 |
| NLS0020 | 85.8*** | 59.58 | 51.26 |
| NLS0066 | 84.3*** | 57.77 | 48.73 |
| NLS0089 | 84.7*** | 46.60* | 39.43** |
| NLS0017 + NLS0066 | 84.1*** | 51.02 | 42.90 |

Asterisks indicate statistical significance relative to the control treatment (Base treatment without PPFM) as follows: *$P < 0.10$, $P < 0.05$, *$P < 0.01$.

NLS0089 significantly reduced disease by all metrics, decreasing disease index by 24% relative to the control. The combination of NLS0017 and NLS0066 reduced disease by all metrics, performed best for reduction in FHB disease incidence, and performed better than either strain applied singly. NLS0017 alone also reduced disease by all metrics. NLS0020, which had not shown suppression of FHB in controlled environment trials was included as a negative control, and performed as expected.

Example 5. Suppression of *Rhizoctonia*-Damping Off Disease

PPFMs were tested for their ability to suppress *Rhizoctonia*-damping off disease. For these assays, PPFM strains, a non-treated control, and a positive control (*Pseudomonas fluorescens*) were arranged into three blocks on a 96-well plate, grown for 24 h at 30° C. with shaking at 250 rpm, then stored at −80° C. Frozen stock plates were used to start new cultures as needed. For the *Rhizoctonia* damping off assay, cultures started from −80° C. stocks were grown for 5 days in a 1 mL well-volume 96-well plate in ammonium mineral salts (AMS) medium containing peptone, glutamate as the carbon source, and an appropriate solid substrate for promotion of *Methylobacterium* growth (International Patent Application PCT/US13/4372, filed May 31, 2013).

Growth conditions were 30° C. with shaking on a platform shaker at 250 rpm. Five-hundred uL of PPFM culture from each well of the 96-well plate was pipetted into a correspondingly labeled two mL microcentrifuge tube and three pea seeds (*Pisum sativum* L., cv. Sugar snap; Johnny's Seeds, Maine, USA) were placed in each tube. After peas were placed into a tube, it was capped and shaken to coat seeds with bacterial solution. After c. one hour, seeds were planted into pathogen-infested potting media.

*Rhizoctonia solani* inoculum was prepared by autoclaving a mixture of ground yellow cornmeal and sand two times, then inoculating with agar plugs excised from the advancing edge of fungal cultures less than one-week old. The inoculated cornmeal-sand mixture was incubated for approximately two weeks on a lab benchtop and shaken every few days to evenly disperse inoculum. After two weeks, inoculum was dried overnight in a sterile biological safety food, then stored at 4° C. until use. A small sample from each inoculum batch was plated onto potato dextrose agar at the time of harvest to check for colonization and to ensure that contaminants were not present in the inoculum. Inoculum was incorporated into potting media just before planting at a final rate of 0.73 g inoculum per cup and deionized water was added to potting media at a final rate of 6.25 mL per cup. Pathogen-infested potting media was placed 96 cups, one labeled for each well in the 96-well bacterial culture plate, and the three seeds from the corresponding well seed treatment tube were planted into each cup. Cups were then covered with a lid to create a high humidity environment and placed into a growth chamber with a 14-hour day-length and constant temperature of 27° C. Dixie ice cream cups were used for this experiment because 1) the closed cup prevent risk of cross-contamination between treatments and 2) the cups come with lids that can be used to increase humidity and prevent the need for watering during the experiment.

Plants were rated for disease severity at one week after planting/inoculation. Ratings included pre-emergence damping off, post-emergence damping off, and plant health. Pre-emergence damping off was rated by counting the total number of seeds per pot that did not germinate; post-emergence damping off was rated by counting the number of seeds per pot that were killed shortly after germination; plant health was rated on a 0-5 scale as follows: 0=dead plant; 1=severely stunted/necrotic plant; 2=moderate to severe stunting and necrosis; 3=moderate stunting and/or necrosis; 4=generally healthy plant with small lesions or slight growth delay; 5=healthy plant. For data analysis, the total number of seedlings with damping off and average plant health per pot values were averaged across the three replicates per treatment. These values were compared to the control. Strains for which [strain average−one standard error of the mean] did not overlap with [non-treated control average+one standard error of the mean] were considered to provide disease suppression. Disease rating data is summarized in Table 8 and plant health data is summarized in Table 9.

TABLE 8

*Rhizoctonia* Average Plant Health Ratings

| Treatment | Avg Plant Health Rating ± SEM |
|---|---|
| No treatment control | 0.89 ± 0.59 |
| *Pseudomonas fluorescens* | 0.56 ± 0.29 |
| NLS0017 | 2.67 ± 0.33 |
| NLS0020 | 1.00 ± 0.58 |
| NLS0037 | 1.67 ± 0.38 |
| NLS0038 | 1.44 ± 0.78 |
| NLS0089 | 2.67 ± 0.69 |

$^a$Average calculated from combining plant health scores from three replicate pots per treatment with each pot containing three seedlings. SEM calculated using n = 3 for the three replicate pots.

TABLE 9

*Rhizoctonia* Average Number of Damped-Off Seedlings

| Treatment | Avg Plant Health Rating ± SEM |
|---|---|
| No treatment control | 2.33 ± 0.67 |
| *Pseudomonas fluorescens* | 2.33 ± 0.33 |
| NLS0017 | 0.67 ± 0.33 |

TABLE 9-continued

Rhizoctonia Average Number of Damped-Off Seedlings

| Treatment | Avg Plant Health Rating ± SEM |
|---|---|
| NLS0020 | 2.00 ± 0.58 |
| NLS0037 | 1.33 ± 0.33 |
| NLS0038 | 1.67 ± 0.67 |
| NLS0089 | 0.67 ± 0.33 |

[a]Average calculated by combining seedling counts from three replicate pot per treatment with each pot containing three seedlings. SEM calculated using n = 3 for the three replicate pots.

Cumulative seedling damping off and plant health were measured and analyzed separately. Strains NLS0017 and NLS0089 suppressed overall seedling damping off and increased overall plant health. These *Methylobacterium* spp. strains have potential for use as seed or in-furrow treatments to protect against *Rhizoctonia*-related diseases.

Example 6. Suppression of White Mold (*Sclerotinia sclerotiorum*) in Soybean by PPFMs Two mL frozen PPFM stock solutions at a concentration of approximately $1 \times 10^8$ CFU/mL were thawed to room temperature directly prior to seed treatment. Thawed PPFM stocks were pelleted by centrifuging, washed once with sterile distilled water, then re-suspended in a final volume of 20 mL sterile distilled water. The 20 mL solution was placed in a 50 mL conical tube and 40 soybeans seeds were placed into the tube with the PPFM solution. The tube was placed on its side and agitated every 10 minutes for a total of 30 minutes. After the 30 minute treatment period, excess liquid was decanted and treated seeds were planted immediately.

Seeds were planted into either potting media, field soil, or a 50/50 mix of potting media and field soil, depending on the specific experiment. In all experiments, flats holding 18 pots each were used and the pots containing individual treatments were organized into randomized complete blocks either at planting or just prior to inoculation. Immediately after planting, pots were moved to a greenhouse (75-80° F.; RH 40-90%; 16 h day-length) and grown there for one month. Plants were watered daily and received supplemental fertilizer two times per week.

One-month old plants were inoculated with 5-7 day-old cultures of *Sclerotinia sclerotiorum* grown on potato dextrose agar PDA in the dark. A modified version of the cut petiole inoculation technique was used (Hoffman et al. 2002. Plant Dis. 86:971-980). Briefly, the petiole of the third trifoliate was cut with scissors approximately one inch from the stem. The broad end of a 1000 uL pipet tip was used to excise an agar disk from the outer edge of an *S. sclerotiorum* culture. The tip was then placed over the cut petiole such that the broad end of the pipet tip was in contact with the stem and petiole base and the cut end of the petiole was in contact with the mycelium side of the agar plug. A small piece of parafilm was wrapped around the tip and stem to prevent the tip from falling off. Inoculated plants were incubated in the greenhouse for 7-10 days to allow for disease development prior to rating.

Lesion length and wilt severity were collected as disease metrics. Length of brown or bleached lesions was measured using a ruler. Wilt severity was rated on a 0-5 scale with 0 indicating a completely health plant and 5 indicating a dead plant. The experiment was conducted as a randomized complete block design with nine blocks per experimental repetition and the experiment was repeated three times, for a sample size of 27 experimental units for each treatment group. Data were analyzed using mixed models analysis in JMP v11.2 (SAS Institute; Cary, N.C.). Wilt and lesion length data were analyzed separately. In each case, repetition was included as a random effect and treatment as a fixed effect. Model fitting criteria determined that blocks within repetitions did not contribute significantly and this factor was dropped from final analysis.

Figure 2:
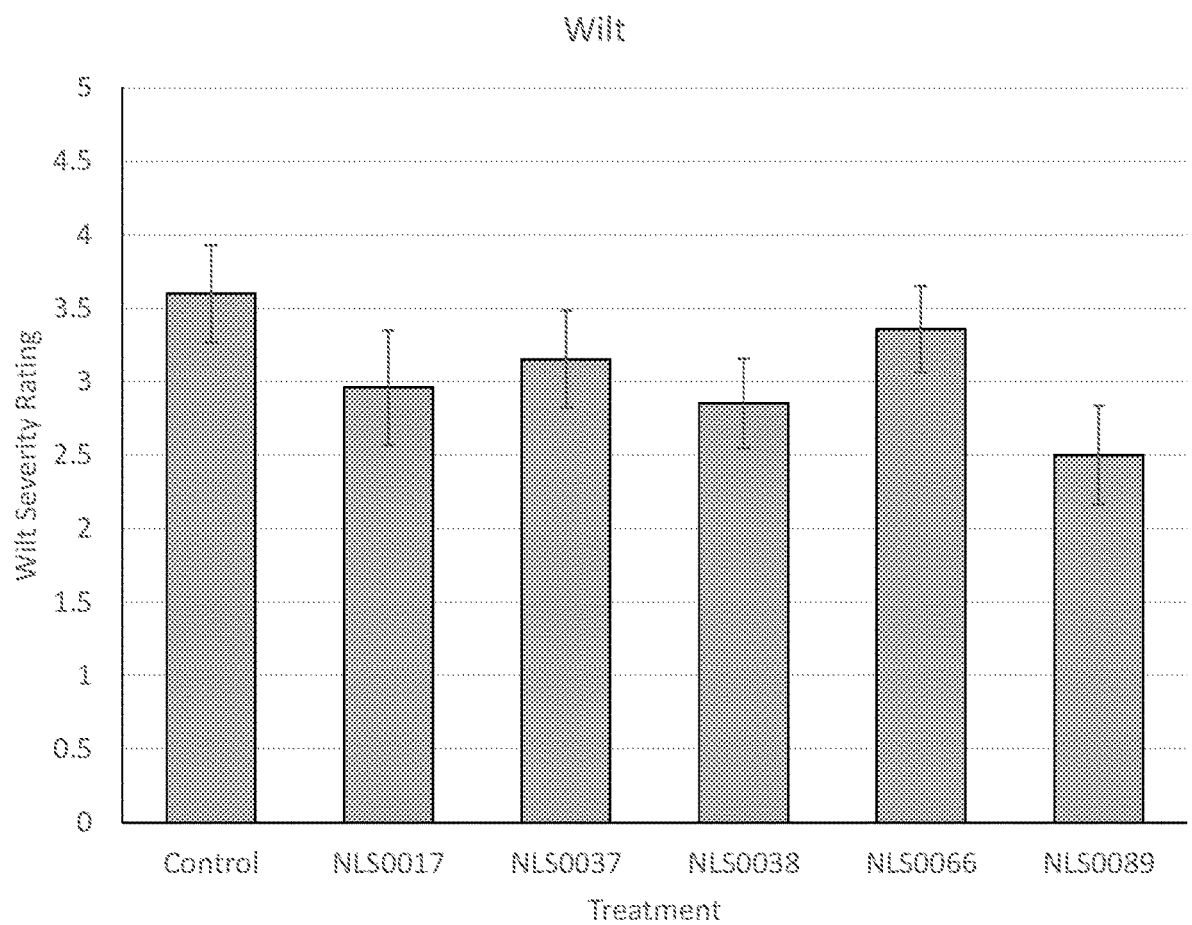
FIG. 2 is a bar chart showing suppression of soybean white mold wilt symptom severity by NLS0089.
Figure 3:
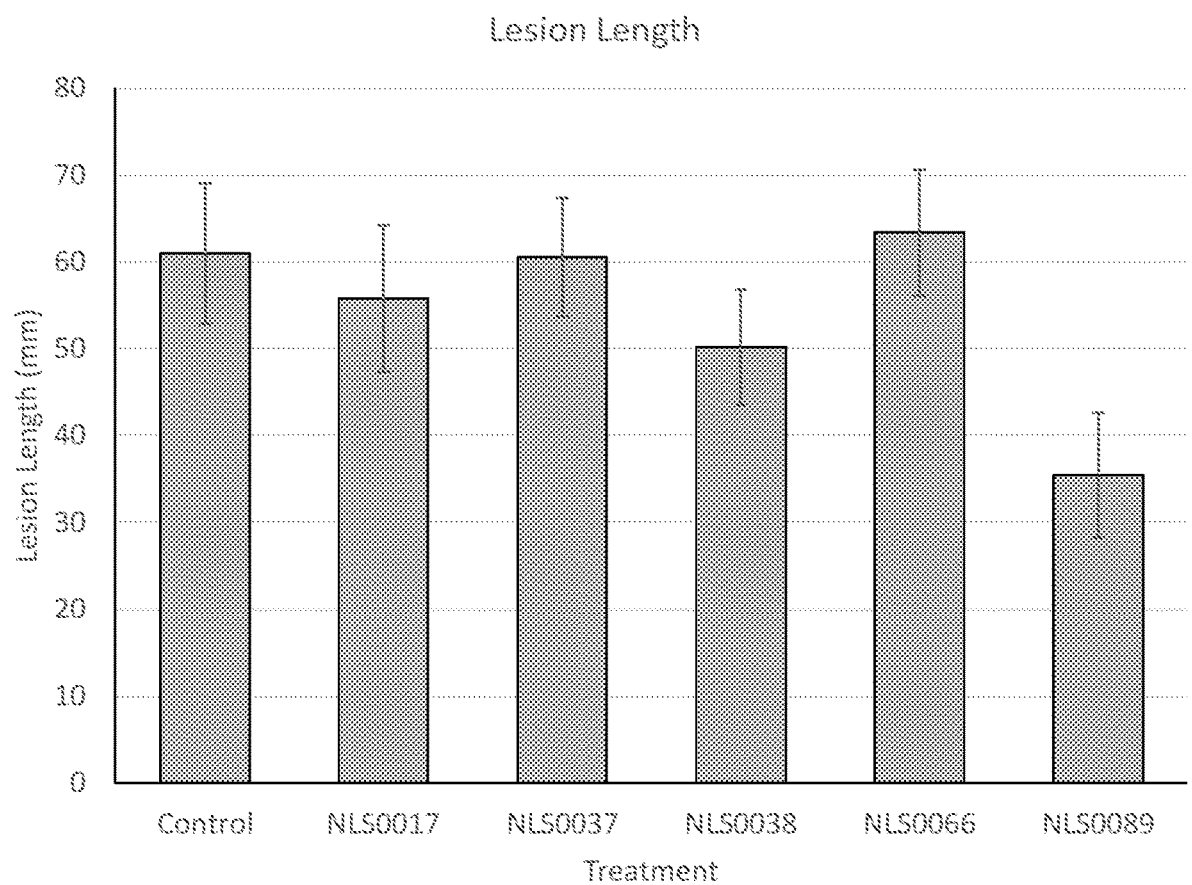
FIG. 3 is a bar chart showing suppression of soybean white mold lesion length development by NLS0089.

Across all three repetitions of the experiment, treatment with NLS0089 significantly reduced both wilt (FIG. 2) and lesion length (FIG. 3) relative to the non-treated control group (Two-sample independent t-test; P<0.01). No other treatment had a significant effect on either disease severity metric. NLS0089 decreased wilt severity by >30% compared to the control group and decreased lesion length relative to the control group by >40%.

Of the five strains tested in this experiment, only NLS0089 significantly reduced both indicators of white mold severity relative to the control group. This strain has the potential to provide suppression of the disease under agronomic conditions and could provide a valuable complement to current white mold disease management practices.

Example 7. Suppression of Soybean Sudden Death Syndrome by PPFMs

Frozen PPFM stock solutions at a concentration of approximately $1 \times 10$ CFU/mL were thawed to room temperature directly prior to seed treatment. Batches of 200 seeds were treated in a laboratory scale seed treater with 1 uL/seed of PPFM concentrate and 0.89 uL/seed of dilute polymer solution (FR1706, Becker Underwood; 6.1 mL polymer diluted in 40 mL deionized water). After treatment, seeds were allowed to dry overnight and were used within one week of treatment. To assess PPFM colonization and viability, aliquots of ten seeds were vortexed for 10 seconds in 10 mL of sterile 0.9% saline solution and 100 uL of the resulting wash solution was plated on PPFM-specific agar plates. Control seeds were treated with stock solutions of PPFM growth medium/polymer solution. The treater was thoroughly cleaned with 70% ethanol between each treatment to prevent cross contamination.

*Fusarium virguliforme* isolates were obtained from the USDA-ARS NRRL culture collection. Cultures were maintained at room temperature on PDA and clarified V8 juice agar. Isolates were also stored at in glycerol at −80° C. and were re-isolated from plants every few months to ensure continued aggressiveness. Inoculum was prepared by soaking sorghum grain overnight in tap water in a 500 mL Erlenmayer flask with a vented lid, draining all water the following day, and autoclaving on a one-hour liquid cycle for two consecutive days. The day after autoclaving was completed, the sterile sorghum grain was inoculated with six agar plugs excised from a 2-4 week-old culture of *Fusarium virguliforme*. Inoculated flasks were incubated on a lab benchtop for approximately two weeks and shaken every few days to evenly disperse inoculum. After two weeks, the colonized grains were plated onto PDA to check for contamination and the inoculum was moved to 4° C. until use. Inoculum was discarded and no longer used for screening assays after one month in storage.

Inoculation occurred at the time of planting. Pots were filled half-full with a 50:50 non-sterile field soil:sand mix and treatments were arranged into a randomized complete block with both inoculated and un-inoculated pots for each PPFM treatment within each block. Inoculated pots received 5 g of sorghum grain inoculum, which was incorporated into the soil mixture prior to the addition of seeds. Two seeds were planted into each pot and then covered with approximately two centimeters of sand:soil mix. For the first two weeks after planting, the experiments were maintained in a growth chamber at 20° C. and watered daily to provide conditions conducive to SDS. After two weeks, the experiments were transferred to a greenhouse at around 23-27° C. and incubated for another two weeks to allow development of aboveground SDS symptoms.

SDS disease severity ratings and plant biomass measurements were taken one month after planting and inoculation. Aboveground disease severity measurements were rated on a 0-5 scale with 0 indicating a completely health plant and 5 indicating a dead plant. After rating, plants were harvested and roots were washed to remove adherent soil before drying. Dry root and shoot biomasses were taken individually to allow for between treatment comparisons for each plant part. Raw data and data on effect size, the difference between inoculated and uninoculated plants for each treatment, were analyzed with Excel and JMP version 11.2 (SAS Institute, Cary, N.C.).

PPFM strains were tested in groups alongside a mock-treated control, which was included in all testing groups. Due to differences between experiments, data for different testing groups are shown separately. In one testing group, NLS0066, strongly reduced the effect size of SDS-related disease metrics, particularly root biomass, indicating that these strains restricted development of disease symptoms and protected plants from growth decreases caused by SDS infection (Tables 10-12). Effect size was calculated as the difference between the inoculated and un-inoculated plants for a given treatment. In the absence of pathogen pressure, NLS0066 had no effect on plant growth.

TABLE 10

Effect Size of PPFM Treatments on SDS Severity[a]

| Treatment | Control Severity ± SEM | Inoculated Severity ± SEM | Effect Size[b] |
|---|---|---|---|
| GlyC-Control | 0.88 ± 0.07 | 2.32 ± 0.04 | −1.44 |
| NLS0038 | 0.92 ± 0.07 | 2.24 ± 0.04 | −1.32 |
| NLS0046 | 0.5 ± 0.07 | 2.46 ± 0.04 | −1.96 |
| NLS0066 | 1.29 ± 0.07 | 2.32 ± 0.03 | −1.03 |

[a]Severity was rated on a 0-5 scale with 0 indicating a fully healthy plant and 5 a dead plant. Sample size of n = 54 per treatment.
[b]A less negative value for effect size indicates a small increase in symptom severity with pathogen inoculation

TABLE 11

Effect Size of PPFM Treatments on Root Weight[a] of SDS-Inoculated Plants

| Treatment | Control Root Weight ± SEM | Inoculated Root Weight ± SEM | Effect Size[b] |
|---|---|---|---|
| GlyC-Control | 960.37 ± 16.57 | 545.99 ± 7.59 | 414.38 |
| NLS0038 | 845.25 ± 14.29 | 540.52 ± 7.67 | 304.73 |
| NLS0046 | 822.73 ± 18.92 | 459.93 ± 7.04 | 362.80 |
| NLS0066 | 737.63 ± 8.84 | 619.58 ± 9.98 | 118.05 |

[a]Root weights given in units of mg. Sample size of n = 54 per treatment.
[b]A smaller effect size indicates a reduced effect of pathogen inoculation.

TABLE 12

Effect Size of PPFM Treatments on Shoot Weight[a] of SDS-Inoculated Plants

| Treatment | Control Root Weight ± SEM | Inoculated Root Weight ± SEM | Effect Size[b] |
|---|---|---|---|
| GlyC-Control | 685.82 ± 11.63 | 455.99 ± 5.19 | 229.83 |
| NLS0038 | 525.57 ± 10.25 | 429.13 ± 3.76 | 96.44 |
| NLS0046 | 497.85 ± 11.25 | 440.84 ± 4.73 | 57.01 |
| NLS0066 | 411.43 ± 7.96 | 448.97 ± 4.23 | −37.54 |

[a]Shoot weights given in units of mg. Sample size of n = 54 per treatment.
[b]A smaller effect size indicates a reduced effect of pathogen inoculation.

Seed treatment of soybean with NLS PPFM strain NLS0066 resulted in strong effects on development of disease caused by the SDS pathogen $F.$ $virguliforme$ under greenhouse conditions. These strains offer potential as biological control agents that could be used singly or in combination with other strains and/or disease mitigation strategies to provide effective and sustainable management of SDS.

Example 8. Corn and Soybean Field Trials Summer of 2015

In the summer of 2015, field trials to evaluate disease suppression in corn and soybeans by PPFMs were performed at two independent locations: Bethel, Mo. and Troy, Ohio. Both trial locations were managed by contract research organizations. NewLeaf Symbiotics personnel visited each site at least twice to ensure proper trial implementation. The same strains and application rates were tested at both locations. The trials were arranged as a split-plot within an RCBD (randomized complete block design) with six replications at the Bethel site and four replications at the Troy site. Treatments for corn are described in Table 13 and treatments for soybean are described in Table 14. In-furrow treatments were applied at a rate of 1,250 mL 10×PPFM concentrate per acre and foliar treatments were applied at a rate of 5,000 mL 10×PPFM concentrate per acre. The split-plot design allowed for the evaluation of in-furrow treatment, foliar treatment, response to sequential PPFM treatments, and interactions between different PPFMs.

TABLE 13

2015 Pathology Corn Field Trial Treatments

| Treatment Number | Whole-plot treatment | Sub-plot treatment |
|---|---|---|
| 1 | Mock | Mock |
| 2 | NLS0020 | Mock |
| 3 | Mock | NLS0020 |
| 4 | NLS0020 | NLS0020 |
| 5 | Mock | NLS0066 |
| 6 | NLS0020 | NLS0066 |

TABLE 14

2015 Pathology Soybean Field Trial Treatments

| Treatment Number | Whole-plot treatment | Sub-plot treatment |
|---|---|---|
| 1 | Mock | Mock |
| 2 | NLS0089 | Mock |
| 3 | Mock | NLS0020 |
| 4 | NLS0089 | NLS0020 |
| 5 | Mock | NLS0066 |
| 6 | NLS0089 | NLS0066 |

At each site, conventional row spacing was used and standard agronomic practices were followed. Corn and soy hybrids with similar genetics but suitable for the specific trial locations were supplied for each site. Sub-plot sizes were no less than four 20' rows. A five-foot border was left between sub-plots to mitigate neighbor effects. Additionally, observations were taken from only the center two rows of each plot. Whole-plots consisted of the four sub-plots plus five foot borders between plots. Trial locations were selected in areas with natural disease pressure and no artificial inoculations were made. As a result, the same diseases were not evaluated at each location. Diseases rated in corn were anthracnose (*Colletotrichum graminicola*), grey leaf spot (*Cercospora zeae-maydis*), and common rust (*Puccinia sorghi*). Diseases rated in soybean were brown spot (*Septoria glycines*) and other foliar diseases. For each disease present, incidence and/or severity ratings were collected and analyzed to determine treatment effects.

Disease ratings and statistical analysis results are reported in Tables 3-5. Due to the different disease ratings and replication number at each site, data from the two trial locations were analyzed separately. Data analyses were performed using SAS JMP software v11.2 (SAS Institute, Cary, N.C.). Data were analyzed according to JMP guidelines for split-plot analysis within the 'Fit Model' function, which uses the REML technique for mixed models. Student's T and Tukey's HSD post hoc tests were applied to determine differences between treatment groups ($\alpha$=0.05). Contrasts were used to make comparisons between specific groups of interest.

TABLE 15

Soybean Foliar Disease - Bethel, Missouri

| Whole-plot (in-furrow) Treatment | Sub-plot (foliar) Treatment | Brown spot severity early (%) | Brown spot severity late (%) | Leaf spot severity early (%) | Leaf spot severity late (%) |
|---|---|---|---|---|---|
| Mock | Mock | 3.00 | 8.33 | 1.67 | 5.50 |
| Mock | NLS0020 | 1.33$^T$ | 4.17$^{T,H}$ | 0.17$^{T,H}$ | 2.00$^{T,H}$ |
| Mock | NLS0066 | 1.67$^T$ | 4.83$^T$ | 0.67$^T$ | 4.17 |
| NLS0089 | Mock | 1.17$^T$ | 5.00$^T$ | 0.17$^T$ | 2.50$^{T,H}$ |
| NLS0089 | NLS0020 | 1.17$^T$ | 5.17$^T$ | 0.33$^{T,H}$ | 2.50$^{T,H}$ |
| NLS0089 | NLS0066 | 1.67 | 5.17$^T$ | 0.33$^{T,H}$ | 4.33 |

$^T$Treatment significantly different from control (Mock, Mock) by Student's T-test ($\alpha$ = 0.05)
$^H$Treatment significantly different from control (Mock, Mock) by Tukey's HSD ($\alpha$ = 0.05)

TABLE 16

Corn Foliar Disease - Bethel, Missouri

| Whole-plot (in-furrow) Treatment | Sub-plot (foliar) Treatment | Anthracnose severity (%) | Gray leaf spot severity early (%) | Gray leaf spot severity late (%) | Common rust severity (%) |
|---|---|---|---|---|---|
| Mock | Mock | 21.17 | 3.17 | 13.00 | 12.17 |
| Mock | NLS0020 | 18.83 | 2.00$^{T,H}$ | 11.33 | 11.67 |
| Mock | NLS0066 | 9.50$^{T,H}$ | 1.83$^{T,H}$ | 10.83$^T$ | 10.50 |
| NLS0020 | Mock | 18.67 | 2.17$^T$ | 11.83 | 10.67 |
| NLS0020 | NLS0020 | 17.83 | 2.00$^T$ | 11.50 | 11.33 |
| NLS0020 | NLS0066 | 9.17$^T$ | 1.00$^{T,H}$ | 9.50$^{T,H}$ | 9.67$^T$ |

$^T$Treatment significantly different from control by Student's T-test ($\alpha$ = 0.05)
$^H$Treatment significantly different from control by Tukey's HSD ($\alpha$ = 0.05)

TABLE 17

Corn Foliar Disease - Troy, Ohio

| Whole-plot (in-furrow) Treatment | Sub-plot (foliar) Treatment | Gray leaf spot severity (%) | Tip dieback severity (%) | Tip dieback incidence (%) | Stalk rot severity (%) |
|---|---|---|---|---|---|
| Mock | Mock | 67.50 | 11.00$^i$ | 0.17$^i$ | 1.55 |
| Mock | NLS0020 | 67.50 | 8.25 | 0.14 | 1.60 |
| Mock | NLS0066 | 62.50 | 12.50 | 0.18 | 1.45 |
| NLS0020 | Mock | 65.00 | 7.50* | 0.12* | 1.85 |
| NLS0020 | NLS0020 | 67.50 | 10.00 | 0.16 | 1.55 |
| NLS0020 | NLS0066 | 60.00 | 9.00 | 0.14 | 1.45 |

$^i$The average across all mock in-furrow treatments was significantly different from the average across all NLS0020 in-furrow treatments by contrast ($\alpha$ = 0.05)
*Treatment significantly different from control (Mock, Mock) by contrast ($\alpha$ = 0.10)

All treatments applied to soybeans demonstrated disease suppression against both brown spot (*Septoria glycines*) and other foliar leaf spot diseases. Foliar application of NLS0020 without in-furrow treatment resulted in the lowest rating for all diseases and was the most effective treatment for suppression of disease relative to the control. Foliar application of NLS0020 following NLS0089 in-furrow treatment also demonstrated disease suppression across all treatments. In-furrow treatment with NLS0089 alone significantly reduced all diseases and had a particularly strong effect against foliar leaf spot diseases.

In corn at the Bethel, Mo. site, in-furrow application of NLS0020 improved the disease suppression provided by NLS0066 foliar applications in all examples. This demonstrates enhanced efficacy through multiple applications of these specific PPFM strains. No application of NLS0020, including in-furrow followed by foliar, provided suppression of more than one disease.

At the Troy, Ohio location, the in-furrow application of NLS0020 alone suppressed both the severity and incidence of tip dieback, which can be indicative of an effect on disease and abiotic stressors. Additionally, all applications of in-furrow NLS0020 combined suppressed tip dieback metrics relative to all mock in-furrow treatments combined, indicating an overall positive effect of NLS0020 in-furrow treatment.

Example 9. Identification of Nucleic Acid Polymorphisms Present in *Methylobacterium* that Inhibit Plant Pathogenic Fungi Whole genome sequencing libraries for the Illumina™ high-throughput sequencing platform are generated for *Methylobacterium* sp. isolates provided in Table 1 using Illumina TRUSEQ™ or NEXTERA™ DNA sample preparation kits (described on the internet sites res.illumina.com/documents/products/datasheets/datasheet_truseq_dna_sample_prepkits.pdf and res.illumina.com/documents/products/datasheets/datasheet_nextera_dna_sample_prep.pdf) using the methods described by the manufacturer. The resultant libraries are then subjected to pyrosequencing (Siqueira J F et al. J Oral Microbiol. 2012; 4: 10.3402/jom.v4i0.10743).

Raw pyrosequencing-generated genomic sequence data are subjected to adaptor- and quality-based trimming for quality control. Whole-genome Shotgun Sequence Assembly (1) is achieved by assembling quality-passed data using the de novo assembler Velvet (2). For gene finding and annotation, reference training data is leveraged from TIGR-FAM (9), Pfam, COG (10), and UniRef100 (11). The rRNAs are identified with RNAmmer (5), protein-coding genes are identified with Glimmer (3) or Maker (6), and tRNAs are identified with tRNAscan-SE (4). Gene functions are assigned with blastx (7), blastp (7), HMMER (8), and InterProScan against comprehensive protein databases described above (Reference Data).

Detection of polymorphisms (SNP or other DNA variations occurring as a result of insertions, deletions, and substitutions (Indels)) in the *Methylobacterium* sp. isolates of Table 1 is performed with BWA (12) and the Samtools suite (on the internet at samtools.sourceforge.net/), structural variation is identified with BreakDancer (on the internet at breakdancer.sourceforge.net/) and CoGE (on the internet at genomevolution.org/CoGe/). Polymorphisms diagnostic for *Methylobacterium* that inhibit plant pathogenic fungi are identified by comparisons of the sequences of *Methylobacterium* isolate NLS0066 that inhibits plant pathogenic fungi but that are absent from one or more *Methylobacterium* isolates NLS0020 and/or NLS0037 that do not inhibit *Fusarium graminearum* infections of plants. Polymorphisms present in *Methylobacterium* isolate NLS0066 that inhibit plant pathogenic fungi but that are absent in *Methylobacterium* isolates NLS0020 and/or NLS0037 that do not inhibit *Fusarium graminearum* are then used to identify other *Methylobacterium* isolates that inhibit plant pathogenic fungi.

REFERENCES FOR EXAMPLE 9

1. Miller J R, Koren S, Sutton G (2010) Assembly algorithms for next-generation sequencing data. Genomics 95: 315-327.
2. Zerbino D R, Birney E (2008) Velvet: algorithms for de novo short read assembly using de Bruijn graphs. Genome Res 18: 821-829.
3. Delcher A L, Bratke K A, Powers E C, Salzberg S L (2007) Identifying bacterial genes and endosymbiont DNA with Glimmer. Bioinformatics 23: 673-679.
4. Lowe T M, Eddy S R (1997) tRNAscan-S E: a program for improved detection of transfer RNA genes in genomic sequence. Nucleic Acids Res 25: 955-964.
5. Lagesen K, Hallin P, Rodland E A, Staerfeldt H H, Rognes T, et al. (2007) RNAmmer: consistent and rapid annotation of ribosomal RNA genes. Nucleic Acids Res 35: 3100-3108.
6. Cantarel B, Korf I, Robb S, et al. (2008) MAKER: An easy-to-use annotation pipeline designed for emerging model organism genomes. Genome Research 18: 188-196.
7. Altschul S F, Madden T L, Schaffer A A, Zhang J, Zhang Z, et al. (1997) Gapped BLAST and PSI-BLAST: a new generation of protein database search programs. Nucleic Acids Res 25: 3389-3402.
8. Eddy S R (2009) A new generation of homology search tools based on probabilistic inference. Genome Inform 23: 205-211.
9. Haft D H, Selengut J D, White O (2003) The TIGRFAMs database of protein families. Nucleic Acids Res 31: 371-373.
10. Tatusov R L, Fedorova N D, Jackson J D, Jacobs A R, Kiryutin B, et al. (2003) The COG database: an updated version includes eukaryotes. BMC Bioinformatics 4: 41.
11. Suzek B E, Huang H, McGarvey P, Mazumder R, Wu C H (2007) UniRef: comprehensive and non-redundant UniProt reference clusters. Bioinformatics 23: 1282-1288.
12. Li H. and Durbin R. (2009) Fast and accurate short read alignment with Burrows-Wheeler Transform. Bioinformatics, 25:1754-60.

Example 10. Identification of Orthologous Genes Present in *Methylobacterium* sp. that can Inhibit Plant Pathogenic Fungi The PPFM strains listed in Table 1 (NLS066, NLS0020, NLS0037) and/or other PPFM strains that do or do not inhibit plant pathogenic fungi can be grown on solid agar media comprising Ammonium Mineral Salts (AMS) plus glycerol and peptone at 30° C. for 5 days, essentially as described in co-assigned U.S. Patent Application Publication No. US20130324407 and incorporated herein by reference in its entirety. Genomic DNA can be extracted using MO-BIG (Carlsbad, Calif.) Ultra Clean™ Microbial DNA Isolation kit, and 1 μg of high quality DNA can be used for Illumina Nextera™ XT library preparation followed by Illumina 2×100 paired-end sequencing on a HiSeq2000™ system. Raw Illumina genomic sequence data can be subjected to adaptor- and quality-based trimming for quality control. Whole-genome Shotgun Sequence Assembly can be achieved by assembling quality-passed data using the de novo assembler SPADES (33). For gene finding and annotation, reference training data can be leveraged from TIGRFAM (9), Pfam, COG (10), and UniRef100 (11). The rRNAs can be identified with RNAmmer (5), protein-coding genes can be identified with Glimmer (3) and Maker (6), and tRNAs can be identified with tRNAscan-SE (4). Gene functions can be assigned with blastx (7), blastp (7), HMMER (8), and InterProScan against comprehensive protein databases described above (Reference Data). Detection of polymorphisms (SNP or other DNA variations occurring as a result of insertions, deletions, and substitutions (Indels)) in the *Methylobacterium* sp. isolates can be performed with BWA (12) and the Samtools suite (on the internet at samtools.sourceforge.net/) and the Genome Analysis Toolkit (GATK, on the world wide web internet site "broadinstitute.org/gatk/"), structural variation can be identified with BreakDancer (on the internet at breakdancer.sourceforge.net/) and CoGE (on the internet at genomevolution.org/CoGe/). Such methods for analyzing *Methylobacterium* sp. genomes of isolates that improve tomato production are disclosed in International Patent Application PCT/US2014/068611, which is incorporated herein by reference in its entirety.

Genes that encode open reading frames can be predicted from the assembled whole genomic sequences of NLS0020, NLS0037, and NLS066 essentially as described above. Within and between genome orthologous genes can be clustered using OrthoMCL (available on the world wide web internet site "orthomcl.org/orthomcl/"). Putative functional annotations can be assigned to gene products using BLASTP (available on the internet site "blast.ncbi.nlm.nih.gov/Blast.cgi") against the UniProt database (available on the world wide web internet site "uniprot.org/"). Genes present in individual genomes of the NLS0066 (as shown in Example 1) or other isolate that could inhibit plant pathogenic fungi but that are absent in the genome of NLS0037 and/or NLS0020 (as shown in Example 1) or other isolate that do not inhibit plant pathogenic fungi can be identified in OrthoMCL clusters using custom software.

REFERENCES FOR EXAMPLE 10

1. Miller J R, Koren S, Sutton G (2010) Assembly algorithms for next-generation sequencing data. Genomics 95: 315-327.

2. Zerbino D R, Birney E (2008) Velvet: algorithms for de novo short read assembly using de Bruijn graphs. Genome Res 18: 821-829.
3. Delcher A L, Bratke K A, Powers E C, Salzberg S L (2007) Identifying bacterial genes and endosymbiont DNA with Glimmer. Bioinformatics 23: 673-679.
4. Lowe T M, Eddy S R (1997) tRNAscan-S E: a program for improved detection of transfer RNA genes in genomic sequence. Nucleic Acids Res 25: 955-964.
5. Lagesen K, Hallin P, Rodland E A, Staerfeldt H H, Rognes T, et al. (2007) RNAmmer: consistent and rapid annotation of ribosomal RNA genes. Nucleic Acids Res 35: 3100-3108.
6. Cantarel B, Korf I, Robb S, et al. (2008) MAKER: An easy-to-use annotation pipeline designed for emerging model organism genomes. Genome Research 18: 188-196.
7. Altschul S F, Madden T L, Schaffer A A, Zhang J, Zhang Z, et al. (1997) Gapped BLAST and PSI-BLAST: a new generation of protein database search programs. Nucleic Acids Res 25: 3389-3402.
8. Eddy S R (2009) A new generation of homology search tools based on probabilistic inference. Genome Inform 23: 205-211.
9. Haft D H, Selengut J D, White O (2003) The TIGRFAMs database of protein families. Nucleic Acids Res 31: 371-373.
10. Tatusov R L, Fedorova N D, Jackson J D, Jacobs A R, Kiryutin B, et al. (2003) The COG database: an updated version includes eukaryotes. BMC Bioinformatics 4: 41.
11. Suzek B E, Huang H, McGarvey P, Mazumder R, Wu C H (2007) UniRef: comprehensive and non-redundant UniProt reference clusters. Bioinformatics 23: 1282-1288.
12. Li H. and Durbin R. (2009) Fast and accurate short read alignment with Burrows-Wheeler Transform. Bioinformatics, 25:1754-60.

REFERENCES

Abanda-Nkpwatt, D., M. Musch, J. Tschiersch, M. Boettner, and W. Schwab. 2006. Molecular interaction between *Methylobacterium extorquens* and seedlings: growth promotion, methanol consumption, and localization of the methanol emission site. J. Exp. Bot. 57: 4025-4032.

Broekaert W F, Terras F R, Cammue B P, Vanderleyden J (1990) An automated quantitative assay for fungal growth inhibition. FEMS Microbiology Letters 69: 55-60 Cappellini R A, Peterson J L (1965) Macroconidium formation in submerged cultures by a non-sporulating strain of *Gibberella zeae*. Mycologia 57: 962-966.

Cao, Y-R, Wang, Q., Jin, R-X., Tang, S-K., He, W-X., Lai, H-X, Xu, L-H., and C-L Jiang. 2011. *Methylobacterium soli* sp. nov. a methanol-utilizing bacterium isolated from the forest soil. Antonie van Leeuwenhoek (2011) 99:629-634.

Cappellini R A, Peterson J L (1965) Macroconidium formation in submerged cultures by a non-sporulating strain of *Gibberella zeae*. Mycologia 57: 962-966 Corpe, W. A., and D. V. Basile. 1982. Methanol-utilizing bacteria associated with green plants. Devel. Industr. Microbiol. 23: 483-493.

Corpe, W. A., and S. Rheem. 1989. Ecology of the methylotrophic bacteria on living leaf surfaces. FEMS Microbiol. Ecol. 62: 243-250.

Correll J C, Klittich C J R, Leslie J F (1987) Nitrate nonutilizing mutants of *Fusarium graminearum* and their use in vegetative compatibility tests. Phytopathology 77: 1640-1646.

Green, P. N. 2005. *Methylobacterium*. In Brenner, D. J., N. R. Krieg, and J. T. Staley (eds.). "Bergey's Manual of Systematic Bacteriology. Volume two, The Proteobacteria. Part C, The alpha-, beta-, delta-, and epsilonproteobacteria." Second edition. Springer, New York. Pages 567-571.

Green, P. N. 2006. *Methylobacterium*. In Dworkin, M., S. Falkow, E. Rosenberg, K.-H. Schleifer, and E. Stackebrandt (eds.). "The Prokaryotes. A Handbook on the Biology of Bacteria. Volume 5. Proteobacteria: Alpha and Beta Subclasses." Third edition. Springer, New York. Pages 257-265.

Holland, M. A. 1997. *Methylobacterium* and plants. Recent. Res. Devel. in Plant Physiol. 1: 207-213.

Holland, M. A., and J. C. Polacco. 1994. PPFMs and other covert contaminants: Is there more to plant physiology than just plant? Annu. Rev. Plant Physiol. Plant Mol. Biol. 45: 197-209.

Kutschera, U. 2007. Plant-associated methylobacteria as co-evolved phytosymbionts. A hypothesis. Plant Signal Behav. 2: 74-78.

Lidstrom, M. E. 2006. Aerobic methylotrophic prokaryotes. In Dworkin, M., S. Falkow, E. Rosenberg, K.-H. Schleifer, and E. Stackebrandt (eds.). "The Prokaryotes. A Handbook on the Biology of Bacteria. Volume 2. Ecophysiology and biochemistry." Third edition. Springer, New York. Pages 618-634.

Madhaiyan, M., S. Poonguzhali, H. S. Lee, K. Hari, S. P. Sundaram, and T. M. Sa. 2005. Pink-pigmented facultative methylotrophic bacteria accelerate germination, growth and yield of sugarcane clone Co86032 (*Saccharum officinarum* L.) Biol. Fertil. Soils 41: 350-358.

Madhaiyan, M., S. Poonguzhali, M. Senthilkumar, S. Seshadri, H. Chung, J. Yang, S. Sundaram, and T. Sa. 2004. Growth promotion and induction of systemic resistance in rice cultivar CO-47 (*Oryza sativa* L.) by *Methylobacterium* spp. Bot. Bull. Acad. Sin. 45: 315-324.

Madhaiyan, M., S. Poonguzhali, and T. Sa. 2007. Influence of plant species and environmental conditions on epiphytic and endophytic pink-pigmented facultative methylotrophic bacterial populations associated with field-grown rice cultivars. J Microbiol Biotechnol. 2007 October; 17(10): 1645-54.

Ringler, G. A. 1995. Reaction of soybean to inoculation with *Fuusarium solani*. M S thesis. Univ. of Illinois, Urbana-Champaign.

Roy, K. W., J. C. Rupe, D. E. Hershman, and T. S. Abney. 19997. Sudden death syndrome of soybean, Plant Dis. 81:1100-1111.

Rupe, J. C, E. E. Gbur, and D. M. Marx. 1991. Cultivar responses to sudden death syndrome of soybean. Plant Dis. 75:47-50.

Spelbrink R G, Dilmac N, Allen A, Smith T J, Shah D M, et al. (2004) Differential antifungal and calcium channel-blocking activity among structurally related plant defensins. Plant Physiol 135: 2055-2067.

Stanier, R. Y., N. J. Palleroni, and M. Doudoroff. 1966. The aerobic pseudomonads: A taxonomic study. J. Gen. Microbiol. 43: 159-271.

Sy, A., Giraud, E., Jourand, P., Garcia, N., Willems, A., De Lajudie, P., Prin, Y., Neyra, M., Gillis, M., Boivin-Masson, C., and Dreyfus, B. 2001. Methylotrophic *Meth-* ylobacterium Bacteria Nodulate and Fix Nitrogen in Symbiosis with Legumes. Jour. Bacteriol. 183(1):214-220,
Sy, A., A. C. J. Timmers, C. Knief, and J. A. Vorholt. 2005. Methylotrophic metabolism is advantageous for *Methylobacterium extorquens* during colonization of *Medicago truncatula* under competitive conditions. Appl. Environ. Microbiol. 71: 7245-7252.
Vogel, H. J., and D. M. Bonner. 1956. Acetylornithinase of *Escherichia coli*: Partial purification and some properties. J. Biol. Chem. 218: 97-106.
Vogel, H. J. 1956. A convenient growth medium for *Neurospora* (Medium N). Microbial Genet Bull 13: 42-43
Whittenbury, R., S. L. Davies, and J. F. Wilkinson. 1970. Enrichment, isolation and some properties of methane-utilizing bacteria. J. Gen. Microbiol. 61: 205-218.
Wrather, J. A. 2010. Soybean disease loss estimates for the United States 1996-2010. Missouri Agric. Res. Sta., Delta Research Center. http://aes.missouri.edu/delta/research/soyloss.htm The inclusion of various references herein is not to be construed as any admission by the Applicant that the references constitute prior art. Applicants expressly reserve their right to challenge any allegations of unpatentability of inventions disclosed herein over the references included herein.

Having illustrated and described the principles of the present disclosure, it should be apparent to persons skilled in the art that the disclosure can be modified in arrangement and detail without departing from such principles.

Although the materials and methods of this disclosure have been described in terms of various embodiments and illustrative examples, it will be apparent to those of skill in the art that variations can be applied to the materials and methods described herein without departing from the concept, spirit and scope of the disclosure. All such similar substitutes and modifications apparent to those skilled in the art are deemed to be within the spirit, scope and concept of the disclosure as defined by the appended claims or otherwise disclosed herein.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11278029B2). An electronic copy of the "Sequence Listing" will also be available from the USPTO upon request and payment of the fee set forth in 37 CFR 1.19(b)(3).

What is claimed is:

1. A method for suppressing a disease caused by a plant pathogenic fungus, wherein said method comprises applying a composition comprising a *Methylobacterium* strain comprising NLS0089 (NRRL B-50933) to a plant or a plant part in an amount that provides for reduction of incidence and/or severity of disease caused by said plant pathogenic fungus in said plant, plant part, or a plant grown from the plant part relative to incidence and/or severity of disease in a control plant, control plant part, or control plant grown from the control plant part that had not received an application of said composition, wherein the plant pathogenic fungus is selected from the group consisting of a *Rhizoctonia* sp., a *Fusarium* sp., a *Pythium* sp., a *Septoria* sp., a *Cercospora* sp., and a *Sclerotinia* sp.

2. The method of claim 1, wherein said composition further comprises *Methylobacterium* strain NLS0017 (NRRL B-50931) and/or *Methylobacterium* strain NLS0020 (NRRL B-50930).

3. The method of claim 1, wherein said *Methylobacterium* is at a titer of at least about $5\times10^7$ colony-forming units per gram, or at least about $5\times10^7$ colony-forming units per milliliter.

4. The method of claim 1, wherein said plant part is selected from the group consisting of a leaf, a stem, a flower, a root, a tuber, and a seed.

5. The method of claim 4, wherein said plant part is a seed, and wherein $1.0\times10^3$, $1.0\times10^4$, $1.0\times10^5$ to about $1.0\times10^7$, $1.0\times10^8$, $1.0\times10^9$, or $1.0\times10^{10}$ CFU of said *Methylobacterium* is applied to said seed.

6. The method of claim 1, wherein mycotoxin levels in said plant or plant part are reduced by at least 50%, at least 75%, at least 85%, or at least 95% relative to a plant part obtained from the control plant, plant part, or plant obtained therefrom.

7. The method of claim 1, wherein said composition is an essentially dry product having 5% or less water content.

8. The method of claim 1, wherein said plant is selected from the group consisting of a rice, soybean, peanut, tomato, wheat, corn, barley, millet, sorghum, oat, and rye plant.

9. The method of claim 1, wherein the plant pathogenic fungus is a *Rhizoctonia* sp.

10. The method of claim 1 wherein said plant or plant part is at least partially coated with said composition.

11. The method of claim 1, wherein the plant is selected from the group consisting of a *Brassica*, alfalfa, sunflower, safflower, tobacco, potato, cotton, sweet potato, cassava, coffee, coconut, pineapple, citrus, cocoa, tea, banana, avocado, fig, guava, mango, olive, papaya, cashew, macadamia, almond, sugar beet, sugarcane, lettuce, green bean, lima bean, pea, cucurbit, ornamental, conifer and turfgrass plant.

12. The method of claim 10, wherein the plant part is a plant seed.

13. The method of claim 12, wherein the seed is from a cereal plant selected from the group consisting of a rice, wheat, corn, barley, millet, sorghum, oat, and rye plant.

14. The method of claim 1, wherein the composition further comprises an additional active selected from the group consisting of an insecticide, a fungicide, a nematocide, a biopesticide, and a beneficial microbe.

15. The method of claim 14, wherein the composition further comprises a pesticide selected from the group consisting of metalaxyl, ipconazole, and imidacloprid.

16. The method of claim 1 wherein said plant is treated by applying said *Methylobacterium* as a spray or as a seed treatment.

17. The method of claim 1, wherein said disease is a foliar disease and wherein the plant is a corn, wheat or soybean plant.

18. The method of claim 17, wherein said disease is a foliar disease caused by a *Septoria* sp., or a *Cercospora* sp.

19. The method of claim 1, wherein said disease is white mold and said plant pathogenic fungus is a *Sclerotinia* sp.

20. The method of claim 1, wherein said plant pathogenic fungus is a *Pythium* sp.

21. The method of claim 1, wherein the plant pathogenic fungus is a *Septoria* sp.

22. The method of claim 1, wherein the plant pathogenic fungus is a *Cercospora* sp.

23. The method of claim 1, wherein the plant pathogenic fungus is a *Fusarium* sp.

* * * * *